US007247706B2

(12) United States Patent
Groppi, Jr. et al.

(10) Patent No.: US 7,247,706 B2
(45) Date of Patent: Jul. 24, 2007

(54) DOUBLE MUTANT ALPHA-7 NICOTINIC ACETYLCHOLINE RECEPTORS

(75) Inventors: Vincent E. Groppi, Jr., Kalamazoo, MI (US); Mitchell B. Berkenpas, Byron Center, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/740,083

(22) Filed: Dec. 18, 2003

(65) Prior Publication Data

US 2004/0132187 A1 Jul. 8, 2004

Related U.S. Application Data

(63) Continuation of application No. 09/579,250, filed on May 25, 2000, now Pat. No. 6,693,172.

(60) Provisional application No. 60/136,174, filed on May 27, 1999.

(51) Int. Cl.
C07K 14/47 (2006.01)
C12N 5/10 (2006.01)
C12N 1/19 (2006.01)
C12N 1/21 (2006.01)

(52) U.S. Cl. ............... 530/350; 435/252.3; 435/254.2; 435/325; 435/365

(58) Field of Classification Search ............... None
See application file for complete search history.

(56) References Cited

U.S. PATENT DOCUMENTS

| 5,837,489 | A | * | 11/1998 | Elliott et al. ............... 435/69.1 |
| 6,022,704 | A | | 2/2000 | Elliott et al. |
| 6,323,000 | B2 | | 11/2001 | Briggs et al. ............... 435/69.1 |
| 6,693,172 | B1 | * | 2/2004 | Groppi et al. ............... 530/351 |
| 2001/0006796 | A1 | | 7/2001 | Briggs et al. ............... 435/69.1 |
| 2003/0073161 | A1 | | 4/2003 | Briggs et al. ............... 435/69.1 |

FOREIGN PATENT DOCUMENTS

| EP | 0367566 | 10/1989 |
| WO | WO 91/18982 | 12/1991 |
| WO | WO 93/13423 | 7/1993 |
| WO | WO 94/20617 | 3/1994 |
| WO | WO98/28331 | 7/1998 |
| WO | WO 98/28331 | 7/1998 |
| WO | WO 99/18438 | 9/1998 |

OTHER PUBLICATIONS

Hurst et al. 2005. The Journal of Neuroscience. 25(17): 4396-4405.*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Wang et al. (Nuc. Acids Res. 27: 4609-4618, 1999; p. 4617).*
Kaufman et al (Blood 94: 3178-3184, 1999).*
Agnew, W.S., et al., *Purification of the tetrodotoxin-binding component associated with the voltage-sensitive sodium channel from Electrophorus electricus electroplax membranes*. Proc Natl Acad Sci U S A, 1978. 75(6): p. 2606-10.
Agnew, W.S., et al., *Identification of a large molecular weight peptide associated with a tetrodotoxin binding protein from the electroplax of Electrophorus electricus*. Biochem Biophys Res Commun, 1980. 92(3): p. 860-6.
Ausubel, et al, ed., Short Protocols in Molecular Biology, 2nd edition, John Wiley & Sons, publishers, p. 16-49, 1992.
Bertrand, D., et al., *Mutations at two district sites within the channel domain M2 alter calcium permeability of neuronal α7 nicotinic receptor*, Proc. Natl, Acad. Sci, 90, pp. 6971-6975, 1993.
Brown, A.M., et al., *Ion permeation and conduction in a human recombinant 5-HT3 receptor subunit (h5-HT3A)*. J Physiol (Lond), 1998. 507(Pt 3): p. 653-65.
Camacho, P., et al., *The epsilon subunit confers fast channel gating on multiple classes of acetylcholine receptors*. J Neurosci, 1993. 13(2): p. 605-13.
Catterall, W.A., *Molecular properties of voltage-sensitive sodium channels*. Annu Rev Biochem, 1986. 55: p. 953-85.
Catterall, W.A., *Cellular and molecular biology of voltage-gated sodium channels*. Physiol Rev, 1992. 72(4 Suppl): p. S15-48.
Catterall, W. and P.N. Epstein, *Ion channels*. Diabetologia, 1992. 35 Suppl 2: p. S23-33.
Cooper, S.T. and N.S. Millar, *Host cell-specific folding and assembly of the neuronal nicotinic acetylcholine receptor alph7 subunit*. J Neurochem, 1997. 68(5): p. 2140-51.
Cosman, et al., *High Level Stable Expression of Human Interleukin-2 Receptors in Mouse Cells Geneerates only Low Affinity Interleukin-2 Binding Sites*, Mol. Immunol. 23:935 (1986).
Cosman et al., *Cloning, sequence and expression of human intereukin-2 receptor*, Nature 312:768 (1984).
Dickenson, A.H., *A cure for wind up: NMDA receptor antagonists as potential analgesics*. Trends Pharmacol Sci, 1990. 11(8): p. 307-9.
Dineley, K.T., *Amino acid determinants of alpha-7 nicotinic acetylocholine receptor surface expression*, J. Biol. Chem., 275(18), p. 13974-13985, 2000.
Earle, W., *Earle's Balanced Salts*, Sigma 1997 Cell Culture Catalogue, 1997, Sigma Company, Amsterdame XP002157176.

(Continued)

Primary Examiner—Ruixiang Li
Assistant Examiner—Zachary C. Howard
(74) Attorney, Agent, or Firm—Steven T. Zelson; E. Victor Donahue

(57) ABSTRACT

The invention relates ton novel methods for measuring ion channel transmission and methods and compositions useful in the indentification of ligand gated channel agonists and modulators.

4 Claims, 10 Drawing Sheets

OTHER PUBLICATIONS

Eisele, J.L., et al., *Chimaeric nicotinic-serotonergic receptor combines distinct ligand binding and channel specificities*. Nature, 1993. 366(6454): p. 479-83.

Fisher, M. and J. Bogousslavsky, *Evolving toward effective therapy for acute ischemic stroke*. Jama, 1993. 270(3): p. 360-4.

Gluzman et al., *SV 40-Transformed Simian Cells Support the Replication of Early SV40 Mutants*, Cell 23:175 (1981).

Hartshorne, R.P. and W.A. Catterall, *The sodium channel from rat brain. Purification and subunit composition*. J Biol Chem, 1984. 259(3): p. 1667-75.

Hille, B., *Ionic Channels of Excitable Membranes*, 1992, p. 252-257.

Holladay, M.W., et al., Identification and initial structure-activity relationships of (R)-5-(2-azetidinylmethoxy)-2-chloropyridine (ABT-594), a potent, orally active, non-opiate analgesic agent acting via neuronal nicotinic acetylcholine receptors. J Med Chem, 1998. 41(4): p. 407-12.

Holladay, M. W., et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett, 1998. 8(19): p. 2797-802.

Johnson, J.W. and P. Ascher, Glycine potentiates the NMDA response in cultured mouse brain neurons. Nature, 1987. 325(6104): p. 529-31.

Kraner, S.D., J.C. Tanaka, and R.L. Barchi, Purification and functional reconstitution of the voltage-sensitive sodium channel from rabbit T-tubular membranes. J Biol Chem, 1985. 260(10): p. 6341-7.

Kuntzweiler, et al., Rapid Assessment of Ligand Actions with Nicotinic Acetylcholine Receptors Using Calcium Dynamics and FLIPR, Drug Development Research 44: p. 14-20, 1998.

Kurosaki, T., et al., Functional properties of nicotinic acetylcholine receptor subunits expressed in various combinations. FEBS Lett, 1987. 214(2): p. 253-8.

Luckow and Summers, Trends in the Development of Baculovirus Expression Vectors, Bio/Technology 6: p. 47-55 (1988).

McCleskey, E.W., et al., Omega-conotoxin: direct and persistent blockade of specific types of calcium channels in neurons but not muscle. Proc Natl Acad Sci USA, 1987. 84(12): p. 4327-31.

Maricq, Andres V., et al., Primary Structure and Functional Expression of the $5HT_3$ Receptor, a Serotonin-Gated Ion Channel., Science, 254, pp. 432-437, 1991.

Nowycky, M.C., A.P. Fox, and R.W. Tsien, Three types of neuronal calcium channel with different calcium agonist sensitivity. Nature, 1985. 316(6027): p. 440-3.

Okayama and Berg, A cDNA Cloning Vector that Permits Expression of cDNA Inserts in Mammalian Cells, (Mol. Cell. Biol. 3:280 (1983).

Peng, X., et al., Human alpha 7 acetylcholine receptor: cloning of the alpha 7 subunit from the SH-SY5Y cell line and determination of pharmacological properties of native receptors and functional alpha 7 homomers expressed in *Xenopus oocytes*. Mol. Pharmacol, 1994. 45(3): p. 546-54.

Picciotto, MR, et al., Nicotinic Receptors in the Brain: Links between Molecular Biology and Behavior, Neuropsychopharmacology 2000, 22(5), p. 451-465.

Ransom, R.W. and N.L. Stec, Cooperative modulation of [3H]MK-801 binding to the N-methyl-D- aspartate receptor-ion channel complex by L-glutamate, glycine, and polyamines. J Neurochem, 1988. 51(3): p. 830-6.

Richardson, B.P., et al., Identification of serotonin M-receptor subtypes and their specific blockade by a new class of drugs. Nature, 1985. 316(6024): p. 126-31.

Sanchez, JEG, et al., Susceptibility of Helicobacter pylori to mupirocin, oxazolidinones, quinupristin/dalfopristin and new quinolones, j of Antimicrobial Chemotherapy (2000) 46, p. 283-285.

Sher, E. and F. Clementi, Omega-conotoxin-sensitive voltage-operated calcium channels in vertebrate cells. Neuroscience, 1991. 42(2): p. 301-7.

Schroeder et al., *FLIPR: A New Instrument for Accurate, High Throughput Optical Screening, Journal of Biomolecular Screening*, 1996, 1(2) pp. 75-80 (incorporated herein by reference).

Tanaka, J.C., J.F. Eccleston, and R.L. Barchi, Cation selectivity characteristics of the reconstituted voltage-dependent sodium channel purified from rat skeletal muscle sarcolemma. J Biol Chem, 1983. 258(12): p. 7519-26.

Watkins, J.C. and G.L. Collingridge, *The NMDA Receptor*. First ed. 1989: IRL Press.

Wei, A., et al., K+ current diversity is produced by an extended gene family conserved in Drosophila and mouse, Science, 1990. 248(4955): p. 599-603.

Yamaguchi, S., S.D. Donevan, and M.A. Rogawski, Anticonvulsant activity of AMPA/kainate antagonists: comparison of GYKI 52466 and NBOX in maximal electroshock and chemoconvulsant seizure models. Epilepsy Res, 1993. 15(3): p. 179-84.

Yang, J., Ion permeation through 5-hydroxytryptamine-gated channels in neuroblastoma N18 cells Gen Physiol, 1990. 96(6): p. 1177-98.

Chavez-Noriega, L.E. et al., "Pharmacological Characterization of Recombinant Human Neuronal Nicotinic Acetylcholine Receptors $h\alpha 2\beta 2$, $h\alpha 2\beta 4$, $h\alpha 3\beta 2$, $h\alpha 3\beta 4$, $h\alpha 4\beta 2$, $h\alpha 4\beta 4$ and $h\alpha 7$ Expressed in *Xenopus* Oocytes," J. of Pharmacology and Experimental Therapeutics 280:346-356 [1997].

Dinsley, K.T., Patrick, J.W., "Surface receptor expression determinants: Mechanism." Society for Neuroscience Abstracts—Abstract 332.17, 24(1-2) [1998], 838. 28th Annual Meeting for the Society for Neuroscience, Part 1, Los Angeles, California, USA, Nov. 7-12, 1998.

Elliott, K.J. et al., "Comparative structure of human neuronal $\alpha 2$-$\alpha 7$ and $\beta 2$-$\beta 4$ nicotinic acetylcholine receptor subunits and functional expression of the $\alpha 2$, $\alpha 3$, $\alpha 4$, $\alpha 7$, $\beta 2$ and $\beta 4$ subunits," Journal of Molecular Neuroscience 7:217-228 [1996].

Galzi, J-L, et al., "Functional significance of aromatic amino acids from three peptide loops of the $\alpha 7$ neuronal nicotinic receptor site investigated by site-directed mutagenesis," Federation of European Biochemical Societies 294(3):198-202 [1991].

Gopalakrishnan, M. et al., "Stable expression and pharmacological properties of the human $\alpha_7$ nicotinic acetylcholine receptor," European J. of Pharmacology 290:237-246 [1995].

Sequela et al J Neuroscience 13(2) 597-604 (1993).

Sambrook et al "Molecular Cloning: A Laboratory Manual" 2nd Edition (1989) Cold Spring Harbor Press, USA, pp. 16.2-16.4.

Galzi, J.-L. and Changeux, J.-P. "Review: Neurotransmitter Receptors VI; Neuronal nicotinic receptors: molecular organization and regulations" Neuropharmacology, vol. 34, No. 6, 1995, pp. 563-582.

L. E. Adler et al., Biol. Psychiartry, vol. 32, 607-616 (1992).

M. H. Akabas et al., Biochem., vol. 34, 12496-12500 (1995).

A. Akaike et al., Brain Res., vol. 644, 181-187 (1994).

K. Aoshiba et al., J. Lab. Clin. Med., vol. 127, 186-194 (1996).

M. Ballivet et al., J. Mol. Biol., vol. 258, 261-269 (1996).

C. Beck et al., Neurobiol. Disease, vol. 1 95-99 (1994).

C. Beck et al., Epilepsia, vol. 36, S28 (1995).

D. Bertrand et al., Proc. Natl. Acad. Sci. ( , , USA), vol. 89, 1261-1265 (1992).

D. Bertrand et al., Sem. Neurosci., vol. 7, 75-90 (1995).

R. Blitzer et al., Neurosci. Lett., vol. 119, 207-210 (1990).

Briggs, CP et al., European Journal of Pharmacology 336, (1999) 301-308.

J.-P. Changeux et al., Trends Pharmacol. Sci., vol. 13, 299-301 (1992a).

J.-P. Changeux et al., Q. Rev. Biophys., vol. 25, 395-432 (1992b).

J. Chen et al., Biophys. J., vol. 69, 849-859 (1995).

S. Couturier et al., Neuron., vol. 5, 847-856 (1990).

D. Donnelly-Roberts et al., Brain Res., vol. 719, 36-44 (1996).

A. Engel et al., Ann. Neurol., vol. 40, 810-817 (1996).

A. Ferrer-Montiel et al., FEBS Lett., vol. 324, 185-190 (1993).

G. Filatov et al., Mol. Pharmacol., vol. 48, 379-384 (1995).

R. Freedman et al., J. Neurosci., vol. 13, 1965-1975 (1993).

R. Freedman et al., Proc. Natl. Acad. Sci. (USA), vol. 94, 587-592 (1997).

J. Freeman et al., Nature, vol. 269, 218-222 (1977).

K. Fuxe et al., Clin. Investig., vol. 72, 262-268 (1994).

J.-L. Galzi et al., Nature, vol. 359, 500-505 (1992).
M. Garcia-Guzman et al., Eur. J. Neurosci., vol. 7, 647-655 (1995).
F. Hory-Lee et al., J Neurosci., vol. 15, 6453-6460 (1995).
B. Hunter et al., Neurosci. Lett., vol. 168, 130-134 (1994).
K. Imoto et al., Nature, vol. 335, 645-648 (1988).
J. James et al., Behav. Genet., vol. 25, 149-159 (1995).
A. Janson et al., Neurosci., vol. 57, 931-941 (1993).
P. Kienker et al., Biophys. J., vol. 66, 325-334 (1994).
R. Krause et al., J. Physiol. (London), vol. 489, 779-790 (1995).
S. Leonard et al., Schizophr. Bull., vol. 22, 431-445 (1996).
V. Luntz-Leybman et al., Brain Res., vol. 587, 130-136 (1992).
P. Marin et al., NeuroReport, vol. 5, 1977-1980 (1994).
E. Martin et al., Drug. Dev. Res., vol. 31, 135-141 (1994).
C. Newland et al., J. Physiol. (London), vol. 487P, p. 208 (1995a).
C. Newland et al., J. Physiol. (London), vol. 489, 767-778 (1995b).
A. Owen et al., NeuroReport, vol. 6, 2269-2272 (1995).
P. Pugh et al., J. Neurosci., vol. 14, 889-896 (1994).
M. Quik et al., Brain Res., vol. 655, 161-167 (1994).

F. Revah et al., Nature, vol. 353, 846-849 (1991).
I. Rinner et al., Biochem. Biophys. Res. Commun., vol. 203, 1057-1062 (1994).
S. Sawada et al., Neurosci. Res., vol. 20, 317-322 (1994a).
S. Sawada et al., Neurosci. Res., vol. 20, 323-329 (1994b).
S. Sine et al., Neuron, vol. 15, 205-211 (1995).
O. Steinlein et al., Nature Genetics, vol. 11, 201-203 (1995).
O. Steinlein et al., Am. J. Med. Genet., vol. 74, 199-201 (1997).
K. Stevens et al., Neuropsychopharmacol., vol. 15, 152-162 (1996).
J. Sullivan et al., Soc. Neurosci. Abstr., vol. 22, 1263 (1996).
S. Tamamizu et al., Cell. Mol. Neurobiol., vol. 15, 427-438 (1995).
M. Treinin et al., C. elegans. Neuron, vol. 14, 71-877 (1995).
A. Villarroel et al., Proc. R. Soc. Lond. [Biol.], vol. 243, 69-74 (1991).
M. Wayner et al., Peptides, vol. 17, 1127-1133 (1996).

* cited by examiner

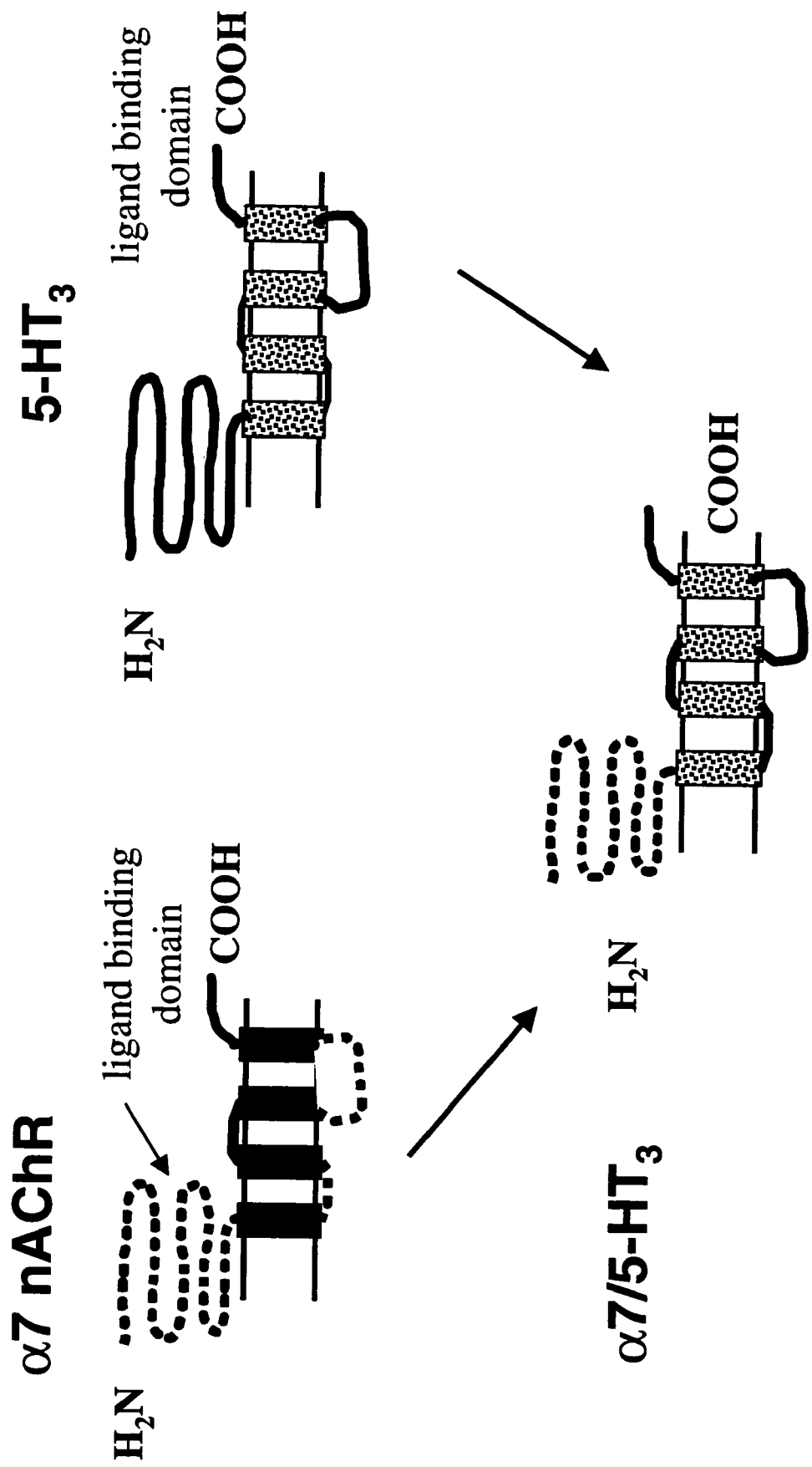

Figure 2

GEFQRKLYKELVKNYNPLERPVANDSQPLTVYFSLLQI
MDVDEKNQVLTTNIWLQMSWTDHYLQWNVSEYPGVKTVRF
PDGQIWKPDILLYNSADERFDATFHTNVLVNSSGHCQYLP
PGIFKSSCYIDVRWFPFDVQHCKLKFGSWSYGGWSLDLQM
QEADISGYIPNGEWDLVGIPGKRSERFYECCKEPYPDVTF
TVIIRRRFYAVSLLPSIFLMVVDIVGFCLPPDSGERV
SFKITLLGYSVFLIIVSDTLPATIGTPLIGVYFVVCMAL
LVISLAETIFIVRLVHKQDLQRPVPDWLRHLVLDRIAWIL
CLGEQPMAHRPPATFQANKTDDCSGSDLLPAMGNHCSHVG
GPQDLEKTPRGRGSPLPPPREASLAVRGLLQELSSIRHFL
EKRDEMREVARDWLRVGYVLDRLLFRIYLLAVLAYSITLV
TLWSIWHYS.

DOUBLE MUTANT ALPHA-7 NICOTINIC ACETYLCHOLINE RECEPTORS

CROSS REFERENCE TO RELATED APPLICATION

The present application is a continuation of U.S. application Ser. No. 09/579,250, filed May 25, 2000 and now U.S. Pat. No. 6,693,172, which claims benefit under 35 USC section 119(e) of U.S. Provisional Patent Application No. 60/136,174 filed May 27, 1999.

FIELD OF THE INVENTION

The invention relates to a novel methods for measuring cellular ion channel transmission and methods and compositions useful in the identification of ligand gated ion channel agonists and modulators.

BACKGROUND OF THE INVENTION

Ion Channels

Ion channel proteins form hydrophilic pores that extend across the cellular lipid bilayer; when these pores are open, they allow specific molecules (usually inorganic ions of appropriate size and charge) to pass through them and thereby cross the membrane.

Channel proteins which are concerned specifically with inorganic ion transport are referred to as ion channels, and include ion channels for sodium, potassium, calcium, and chloride ions. Ion channels which open in response to a change in the voltage across the membrane are referred to as voltage gated ion channels (or voltage-dependent ion channels). Ion channels which open in response to the binding of a ligand to the channel protein are referred to as ligand gated ion channels.

The present invention describes new ion channels and provides methods and compositions suitable for high throughput screening of ion channels.

DESCRIPTION OF THE INVENTION

Voltage Gated Ion Channels

Voltage Gated Sodium Channel

Voltage gated ion channels are a class of channel proteins that play a major role in cellular electrical excitability. In the majority of excitable tissues, the early depolarization phase of action potentials is mediated by a sodium current via voltage-dependent sodium channels (also known as voltage-gated sodium channels or VGSCs). The sodium channel is one of the most thoroughly characterized of the voltage gated channels.

The primary structures of many sodium channels from a variety of tissues (brain, skeletal muscle and cardiac muscle) and organisms (jellyfish, squid, eel, rat, human) have been identified, and their amino acid sequences show individual regions which are highly conserved over evolution, indicating that voltage-dependent sodium channels belong to a large superfamily of evolutionarily related proteins. All published polypeptide complexes of VGSCs have in common a large, about 260 kDa glycoprotein (the pore forming subunit) which is called the alpha subunit (Agnew et al. 1978; Agnew et al. 1980; Catterall 1986; Catterall 1992). Additional lower molecular weight polypeptides, the beta-subunits, have been found to be associated with sodium channels from mammalian muscle (Kraner et al. 1985; Tanaka et al. 1983) and brain (Hartshorne and Catterall 1984). The large, pore-forming alpha subunit is sufficient for all known functions of VGSCs (Catterall 1992) while the beta subunits modulate some of the functions of the alpha subunit (Catterall 1992).

Voltage Gated Potassium Channels

Voltage-gated potassium channels make up a large molecular family of integral membrane proteins that are fundamentally involved in the generation of bioelectric signals such as nerve impulses. These proteins span the cell membrane, forming potassium-selective pores that are rapidly switched open or closed by changes in membrane voltage. Several chemical entities have been discovered to be potent and specific openers of vascular potassium K+ channels. These include cromakalim and its derivatives and RP 52891. This mechanism is also shared, at least partially, by drugs such as minoxidil, diazoxide, pinacidil and nicorandil. The opening of plasmalemmal K+ channels produces loss of cytosolic K+. This effect results in cellular hyperpolarization and functional vasorelaxation. In normotensive or hypertensive rats, K+ channel activators decrease aortic blood pressure (by producing a directly mediated fall in systemic vascular resistance) and reflexively increase heart rate. K+ channel openers produce selective coronary vasodilatation and afford functional and biochemical protection to the ischemic myocardium.

The structure of a typical voltage-gated potassium channel protein is known to be comprised of six membrane spanning domains in each subunit, each of which is regulated by changes in membrane potential. B. Hille. "Ionic Channels of Excitable Membranes" (Sinauer, Sunderland, Mass., 1992). Voltage-gated potassium channels sense changes in membrane potential and move potassium ions in response to this alteration in the cell membrane potential. Molecular cloning studies on potassium channel proteins has yielded information primarily for members of the voltage-gated family of potassium channels. Various genes encoding these voltage-gated family of potassium channel proteins have been cloned using Drosophila genes derived from both the Shaker, Shaw and Shab loci; Wei, A. et. al., Science (1990) Vol. 248 pp. 599–603.

Voltage Gated Calcium Channels

Voltage-gated calcium channels are present in neurons, and in cardiac, smooth, and skeletal muscle and other excitable cells. These channels are known to be involved in membrane excitability, muscle contraction, and cellular secretion, such as in exocytotic synaptic transmission (McCleskey, et al.,1987). In neuronal cells, voltage-gated calcium channels have been classified by their electrophysiological as well as by their biochemical (binding) properties.

Calcium channels are generally classified according to their electrophysiological properties as Low-voltage-activated (LVA) or High-voltage-activated (HVA) channels. HVA channels are currently known to comprise at least three groups of channels, known as L-, N- and P-type channels (Nowycky, et al., 1985). These channels have been distinguished one from another structurally and electrophysiologically as well as biochemically on the basis of their pharmacology and ligand binding properties. Thus, dihydropyridines, diphenylalkylamines and piperidines bind to the alpha 1 subunit of the L-type calcium channel and block a proportion of HVA calcium currents in neuronal tissue, which are termed L-type calcium currents.

N- or omega-type HVA calcium channels are distinguishable from other calcium channels by their sensitivity to omega conotoxins (omega conopeptides). Such channels are insensitive to dihydropyridine compounds, such as L-type calcium channel blockers nimodipine and nifedipine. (Sher and Clementi, 1991).

Ligand Gated Ion Channel Receptors

Ligand-gated ion channels provide a means for communication between cells of the central nervous system. These channels convert a signal (e.g., a chemical referred to as a neurotransmitter) that is released by one cell into an electrical signal that propagates along a target cell membrane. A variety of neurotransmitters and neurotransmitter receptors exist in the central and peripheral nervous systems. At the present time, numerous families of ligand-gated receptors have been identified and characterized on the basis of sequence identity these include nicotinic acetylcholine, glutamate, glycine, GABA A, 5-HT3, and the purinoceptors. These can be further characterized by whether the gated ion channel transmits cations or anions. Those which form cationic channels include, for example, excitatory nicotinic acetylcholine receptors (nAChRs), excitatory glutamate-activated receptors, the 5-HT3 serotonin receptor, and the purine receptor.

Those which form anionic channels include, for example, the inhibitory GABA and glycine-activated receptors. This discussion will confine itself to those ligand gated ion channel receptors which conduct cations.

5HT$_3$ Receptor

Molecular cloning has indicated that serotonin (5-hydroxytryptamine, also referred to as 5-HT) receptors belong to at least two protein superfamilies: G-protein-associated receptors and ligand-gated ion channel. The 5-HT$_3$ receptor belongs to the family of ligand-gated ion channels. As discussed below the 5-HT$_3$ receptor is primarily a sodium potassium ligand gated ion channel under physiologic conditions. The inflammatory and painproducing effects of serotonin are generally believed to be mediated via 5HT$_3$ receptors on peripheral sensory endings (Richardson, B. P., et al., 1985).

Nicotinic Receptors

The nicotinic acetylcholine receptors (nAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various nicotinic acetylcholine receptor (nAChR) subunits exist, a variety of nAChR compositions (i.e., combinations of subunits) exist. The different nAChR compositions exhibit different specificities for various ligands and are thereby pharmacologically distinguishable. Thus, the nicotinic acetylcholine receptors expressed at the vertebrate neuromuscular junction in vertebrate sympathetic ganglia and in the vertebrate central nervous system have been distinguished on the basis of the effects of various ligands that bind to different nAChR compositions. For example, the elapid alpha-neurotoxins that block activation of nicotinic acetylcholine receptors at the neuromuscular junction do not block activation of some neuronal nicotinic acetylcholine receptors that are expressed on several different neuron-derived cell lines.

Muscle nAChR is a glycoprotein composed of five subunits with the stoichiometry alpha 2 alpha ( gamma or epsilon ) delta. Each of the subunits has a mass of about 50–60 kilodaltons (kd) and is encoded by a different gene.

The alpha 2 beta ( gamma or epsilon ) delta complex forms functional receptors containing two ligand binding sites and a ligand-gated transmembrane channel. Upon interaction with a cholinergic agonist, muscle nicotinic AChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal that signals muscle contraction at the neuromuscular junction.

Functional muscle nicotinic acetylcholine receptors have been formed with alpha beta delta gamma subunits, alpha beta gamma subunits, alpha beta delta subunits, alpha beta gamma subunits or alpha delta subunits, but not with only one subunit (see e.g., Kurosaki et al. 1987;Camacho et al. 1993) In contrast, functional neuronal AChRs (nAChRs) can be formed from alpha subunits alone or combinations of alpha and beta subunits. The larger alpha subunit is generally believed to be the ACh-binding subunit and the lower molecular weight beta subunit is generally believed to be the structural subunit, although it has not been definitively demonstrated that the beta subunit does not have the ability to bind ACh. Each of the subunits which participate in the formation of a functional ion channel are, to the extent they contribute to the structure of the resulting channel, "structural" subunits, regardless of their ability (or inability) to bind ACh.

Neuronal AChRs (nAChRs), which are also ligand-gated ion channels, are expressed in ganglia of the autonomic nervous system and in the central nervous system (where they mediate signal transmission), in post-synaptic locations (where they modulate transmission), and in pre- and extra-synaptic locations (where they may have additional functions). The nAChRs comprise a large family of neurotransmitter regulated ion channels that control neuronal activity and brain function. These receptors have a pentameric structure. The gene family is composed of nine alpha and four beta subunits that co-assemble to form multiple subtypes of receptors that have a distinctive pharmacology. Acetycholine is the endogenous regulator of all of the subtypes, while nicotine non-selectively activates all nAChRs. Known chemical templates have subtype selectivity.

α7 nAChR is a ligand-gated $Ca^{++}$ channel formed by a homopentamer of α7 subunits. α7 nAChR is of particular interest because α7 nAChR agonists increase neurotransmitter release, increase cognition, arousal, attention, learning and memory. α7 nAChR is expressed at high levels in the hippocampus, ventral tegmental area and ascending cholinergic projections from nucleus basilis to thalamocortical areas. Previous studies have established that a α-bungarotoxin (α-btx) binds selectively to this homopetameric, α7 nAChR subtype, and that α7 nAChR has a high affinity binding site for both α-btx and methyllycaconitine (MLA). We have chosen to use α7 nAChR as a model system for high throughput drug screening Glutamate Receptors Glycine also functions in excitatory transmission by modulating the actions of glutamate, the major excitatory neurotransmitter in the central nervous system. (Johnson and Ascher, 1987)

Glutamate binds or interacts with one or more glutamate receptors which can be differentiated pharmacologically into several subtypes. In the mammalian central nervous system (CNS) there are three main subtypes of ionotropic glutamate receptors, defined pharmacologically by the selective agonists N-methyl-D-aspartate (NMDA), kainate (KA), and alpha-amino-3-hydroxy-5-methylisoxazole-4-propionic acid (AMPA). The NMDA receptor has been implicated in a variety of neurological pathologies including stroke, head trauma, spinal cord injury, epilepsy, anxiety, and neurodegenerative diseases such as Alzheimer's Disease (Watkins and Collingridge 1989). A role for NMDA receptors in nociception and analgesia has been postulated as well (Dickenson, 1990). More recently, AMPA receptors have been widely studied for their possible contributions to such neurological pathologies (Fisher and Bogousslavsky,.1993).

When activated by glutamate, the endogenous neurotransmitter, the NMDA receptor permits the influx of extracellular calcium (Ca++) and sodium (Na+) through an associated ion channel. The NMDA receptor allows considerably more influx of Ca++ than do kainate or AMPA receptors and is an example of a receptor-operated Ca++ channel. Normally, the channel is opened only briefly, allowing a localized and transient increase in the concentration of intracellular Calcium (Ca++) which, in turn, alters the functional activity of the cell.

The activity of the NMDA receptor-ionophore complex is regulated by a variety of modulatory sites that can be targeted by selective antagonists. Competitive antagonists, such as the phosphonate AP5, act at the glutamate binding site, whereas noncompetitive antagonists, such as phencyclidine (PCP), MK-801 or magnesium (Mg++), act within the associated ion channel (ionophore). There is also a glycine binding site that can be blocked selectively with compounds such as 7-chlorokynurenic acid. There is evidence suggesting that glycine acts as a co-agonist, so that both glutamate and glycine are necessary to fully elicit NMDA receptor-mediated responses. Other potential sites for modulation of NMDA receptor function include a zinc (Zn<2+>) binding site and a sigma ligand binding site. Additionally, endogenous polyamines such as spermine are believed to bind to a specific site and so potentiate NMDA receptor function (Ransom and Stec,.1988). The potentiating effect of polyamines on NMDA receptor function may be mediated via a specific receptor site for polyamines.

Purinergic Receptors

Purinergic receptors are classified as P1 (adenosine as ligand) and P2 (ATP as ligand). The P2 receptors are subclassified into two broad types-those that are 7-transmembrane receptors that couple to G-proteins (P 2Y , P 2U , P 2T, and perhaps P 2Z. Another major class of purinoceptors are the P2x purinoceptors which are ligand-gated ion channels possessing intrinsic ion channels permeable to Na+, K+, and Ca++. P2x receptors described in sensory neurons are important for primary afferent neurotransmission and nociception. ATP is known to depolarize sensory neurons and plays a role in nociceptor activation since ATP released from damaged cells stimulates P2x receptors leading to depolarization of nociceptive nerve-fiber terminals. ATP-sensitive potassium channels have been discovered in numerous tissues, including kidney, vascular and non-vascular smooth muscle and brain, and binding studies using radiolabeled ligands have confirmed their existence. Opening of these channels causes potassium (K<+>) efflux and hyperpolarizes the cell membrane Ion Channels as Drug Targets Ion channels both ligand gated and voltage gated, are in general excellent and validated drug targets. For some channels however, a functional high throughput screening assay is problematic because expression levels are low and function is hard to measure using standard detection technology for high throughput screening. For those channels which normally conduct a cation other than calcium high througput screening methods are often cumbersome. For calcium conductance however, several rapid assays exist. It would often be desireable to This invention provides the scientist with a detailed description about how to convert a channel normally conducting sodium or potassium under physiologic conditions to one conducting calcium for ease in assay development.

The α7 nAChR discussed above is one ligand gated ion channel that has proved to be a difficult target for developing a functional high throughput screening assay. Native α7 nAChR are not routinely able to be stably expressed in most mammalian cell lines (Cooper and Millar 1997). Repeated attempts by our group to stably express the human α7 nAChR in HRK 293, CHO, COS and SH-EP1 were unsuccessful. While it was possible to identify cell lines that initially expressed functional α7 nAChR, these lines dramatically lost receptor expression with prolonged growth in culture. Under these conditions it was not possible to use these lines for screening purposes. Another feature that makes functional assays of α7 nAChR challenging is that the receptor is rapidly (100 milliseconds) inactivated agonist application. This rapid inactivation greatly limits the functional assays that can be used to measure channel activity One solution to the problem is to engineer the α7 nAChR to have a longer duration of open probability and to have it be expressed better in mammalian cells. We are aware of a report indicating that a chimeric receptor formed between the N-terminal ligand binding domain of the α7 nAChR (AA 1–201) and the pore forming C-terminal domain of the 5-HT$_3$ receptor expressed well in Xenopus oocytes while retaining nicotinic agonist sensitivity (Eisele et al. 1993). Eisele et al (1993) used the N-terminus of the avian (chick) form of the α7 nAChR receptor and the c-terminus of the mouse form of the 5-HT$_3$ gene. The report of Eisele et. al. was interesting to us because we knew from our own studies that the 5-HT$_3$ channels expressed well in most mammalian cells. In addition, we also knew from past studies that 5-HT$_3$ channels inactivated much slower than nicotinic channels. A chimeric receptor prepared from the ligand binding region of α7 nAChR and the pore forming domain of 5-HT$_3$ might express well in mammalian cells and might be easier to measure in a functional assay. However, under physiological conditions the α7 nAChR is a calcium channel while the 5-HT$_3$ receptor is a sodium and potassium channel. Indeed, Eisele et al. teaches that the chicken α7 nAChR/mouse 5-HT$_3$ receptor behaves quite differently than the native α7 nAChR with the pore element not conducting calcium but actually being blocked by calcium ions. The chicken/mouse hybrid of Eisele is also not suitable for accessing compounds for their activity at the human α7 nAChR receptor. The human α7 nAChR has 92% identity with the chicken α7 nAChR, but surprisingly, the pharmacology of the two receptors are different. For example, 1,1-dimethyl-4-phenylpiperazinium is a full agonist at the human receptor and a partial agonist at the chicken receptor (Peng et al 1994). Other large species-specific differences in binding affinity have been noted (Peng et al 1994).

Ligand binding can be accessed in either whole cells or membrane preparations but both kinds of assays are cumbersome. Whole cell assays have been difficult to perform in a high throughput screening format because of the extensive washing and manipulation required to obtain a good signal to noise ratio. Isolated membranes have been used in such assays but also typically require extensive manipulation to prepare the membranes themselves and the assay itself requires extensive manipulation and washing to obtain a favorable signal to noise ratio. Such assays are illustrated in U.S. Pat. No. 6,022,704. A binding assay which could be performed without such required extensive manipulation would be extremely useful.

Within the last few years very precise measurement of cellular fluorescence in a high throughput whole cell assay has become possible with the use of a device marketed by Molecular Devices, Inc. designated "FLIPR" (Schroeder et al. 1996), entire document, full reference provided below, incorporated herein by reference. FLIPR has shown considerable utility in measuring membrane potential of mammalian cells using voltage-sensitive fluorescent dyes but is useful for measuring essentially any cellular fluorescence phenomenon. The device uses low angle laser scanning illumination and a mask to selectively excite fluorescence within approximately 200 microns of the bottoms of the wells in standard 96 well plates. The low angle of the laser reduces background by selectively directing the light to the cell monolayer. This avoids background fluorescence of the surrounding media. This system then uses a CCD camera to image the whole area of the plate bottom to measure the resulting fluorescence at the bottom of each well. The signal measured is averaged over the area of the well and thus measures the average response of a population of cells. The system has the advantage of measuring the fluorescence in each well simultaneously thus avoiding the imprecision of sequential measurement well by well measurement. The system is also designed to read the fluorescent signal from each well of a 96 or 384 well plate as fast as twice a second. This feature provides FLIPR with the capability of making very fast measurements in parallel. This property allows for the measurement of changes in many physiological properties of cells that can be used as surrogated markers to a set of functional assays for drug discovery. FLIPR is also designed to have state of the art sensitivity. This allows it to measure very small changes with great precision.

INFORMATION DISCLOSURE

U.S. Pat. No. 6,022,704, Feb. 8, 2000, DNA and mRNA encoding an alpha 4 subunit of human neuronal nicotinic acetylcholine receptor and cells transformed with same, Elliott, K. J. et. al.

1. Agnew, W. S., et al., *Purification of the tetrodotoxin-binding component associated with the voltage-sensitive sodium channel from Electrophorus electricus electroplax membranes.* Proc Natl Acad Sci USA, 1978. 75(6): p. 2606–10.
2. Agnew, W. S., et al., *Identification of a large molecular weight peptide associated with a tetrodotoxin binding protein from the electroplax of Electrophorus electricus.* Biochem Biophys Res Commun, 1980. 92(3): p. 860–6.
3. Brown, A. M., et al., *Ion permeation and conduction in a human recombinant 5-HT3 receptor subunit (h5-HT3A).* J Physiol (Lond), 1998. 507(Pt 3): p. 653–65.
4. Camacho, P., et al., *The epsilon subunit confers fast channel gating on multiple classes of acetylcholine receptors.* J Neurosci, 1993. 13(2): p. 605–13.
5. Catterall, W. A., *Molecular properties of voltage-sensitive sodium channels.* Annu Rev Biochem, 1986. 55: p. 953–85.
6. Catterall, W. A., *Cellular and molecular biology of voltage-gated sodium channels.* Physiol Rev, 1992. 72(4 Suppl): p. S15–48.
7. Catterall, W. and P. N. Epstein, *Ion channels.* Diabetologia, 1992. 35 Suppl 2: p. S23–33.
8. Cooper, S. T. and N. S. Millar, *Host cell-specific folding and assembly of the neuronal nicotinic acetylcholine receptor alpha7 subunit.* J Neurochem, 1997. 68(5): p. 2140–51.
9. Dickenson, A. H., *A cure for wind up: NMDA receptor antagonists as potential analgesics.* Trends Pharmacol Sci, 1990. 11(8): p. 307–9.
10. Eisele, J. L., et al., *Chimaeric nicotinic-serotonergic receptor combines distinct ligand binding and channel specificities [see comments].* Nature, 1993. 366(6454): p. 479–83.
11. Fisher, M. and J. Bogousslavsky, *Evolving toward effective therapy for acute ischemic stroke.* Jama, 1993. 270(3): p. 360–4.
12. Hartshorne, R. P. and W. A. Catterall, *The sodium channel from rat brain. Purification and subunit composition.* J Biol Chem, 1984. 259(3): p. 1667–75.
13. Hille, B., *Ionic Channels of Excitable Membranes.* 1992.
14. Holladay, M. W., et al., *Identification and initial structure-activity relationships of (R)-5-(2-azetidinylmethoxy)-2-chloropyridine (ABT-594), a potent, orally active, non-opiate analgesic agent acting via neuronal nicotinic acetylcholine receptors.* J Med Chem, 1998. 41(4): p. 407–12.
15. Holladay, M. W., et al., *Structure-activity studies related to ABT-594, a potent nonopioid analgesic agent: effect of pyridine and azetidine ring substitutions on nicotinic acetylcholine receptor binding affinity and analgesic activity in mice.* Bioorg Med Chem Lett, 1998. 8(19): p. 2797–802.
16. Johnson, J. W. and P. Ascher, *Glycine potentiates the NMDA response in cultured mouse brain neurons.* Nature, 1987. 325(6104): p. 529–31.
17. Kraner, S. D., J. C. Tanaka, and R. L. Barchi, *Purification and functional reconstitution of the voltage-sensitive sodium channel from rabbit T-tubular membranes.* J Biol Chem, 1985. 260(10): p. 6341–7.
18. Kurosaki, T., et al., *Functional properties of nicotinic acetylcholine receptor subunits expressed in various combinations.* FEBS Lett, 1987. 214(2): p. 253–8.
19. McCleskey, E. W., et al., *Omega-conotoxin: direct and persistent blockade of specific types of calcium channels in neurons but not muscle.* Proc Natl Acad Sci USA, 1987. 84(12): p. 4327–31.
20. Nowycky, M. C., A. P. Fox, and R. W. Tsien, *Three types of neuronal calcium channel with different calcium agonist sensitivity.* Nature, 1985. 316(6027): p. 440–3.
21. Peng, X., et al., *Human alpha 7 acetylcholine receptor: cloning of the alpha 7 subunit from the SH-SY5Y cell line and determination of pharmacological properties of native receptors and functional alpha 7 homomers expressed in Xenopus oocytes.* Mol Pharmacol, 1994. 45(3): p. 546–54.
22. Ransom, R. W. and N. L. Stec, *Cooperative modulation of [3H]MK-801 binding to the N-methyl-D-aspartate receptor-ion channel complex by L-glutamate, glycine, and polyamines.* J Neurochem, 1988. 51(3): p. 830–6.
23. Richardson, B. P., et al., *Identification of serotonin M-receptor subtypes and their specific blockade by a new class of drugs.* Nature, 1985. 316(6024): p. 126–31.
24. Sher, E. and F. Clementi, *Omega-conotoxin-sensitive voltage-operated calcium channels in vertebrate cells.* Neuroscience, 1991. 42(2): p. 301–7.
25. Tanaka, J. C., J. F. Eccleston, and R. L. Barchi, *Cation selectivity characteristics of the reconstituted voltage-dependent sodium channel purified from rat skeletal muscle sarcolemma. J Biol Chem, 1983. 258(12): p. 7519–26.
26. Watkins, J. C. and G. L. Collingridge, *The NMDA Receptor*. First ed. 1989: IRL Press.
27. Wei, A., et al., *K+ current diversity is produced by an extended gene family conserved in Drosophila and mouse.* Science, 1990. 248(4955): p. 599–603.
28. Yamaguchi, S., S. D. Donevan, and M. A. Rogawski, *Anticonvulsant activity of AMPA/kainate antagonists: comparison of GYKI 52466 and NBQX in maximal electroshock and chemoconvulsant seizure models.* Epilepsy Res, 1993.15(3): p. 179–84.
29. Yang, J., *Ion permeation through 5-hydroxytryptamine-gated channels in neuroblastoma N18 cells.* J Gen Physiol, 1990. 96(6): p. 1177–98.
30. Schroeder et al., FLIPR: *A New Instrument for Accurate, High Throughput Optical Screening, Journal of Biomolecular Screening*, 1996, 1(2) pp. 75–80 (incorporated herein by reference).

BRIEF DESCRIPTION OF THE FIGURES

FIG. 1. Construction of the α7/5-HT$_3$ Chimeric Ligand Gated Ion Channel

FIG. 2 Amino Acid Sequence of the mature cell surface form of the α7/5-HT$_3$ Chimeric Ligand Gated Ion Channel. (mutant α7 receptors of SEQ ID NOS: 10, 12, 14) have same mature amino terminus) Underlined=N-terminal AA (1–201) from human α7 nAChR gene Not underlined=C-terminal AA from mouse 5-HT$_3$ gene Bold font=position of transmembrane domain 1

BRIEF DESCRIPTION OF THE SEQUENCE LISTINGS

Figure 3:
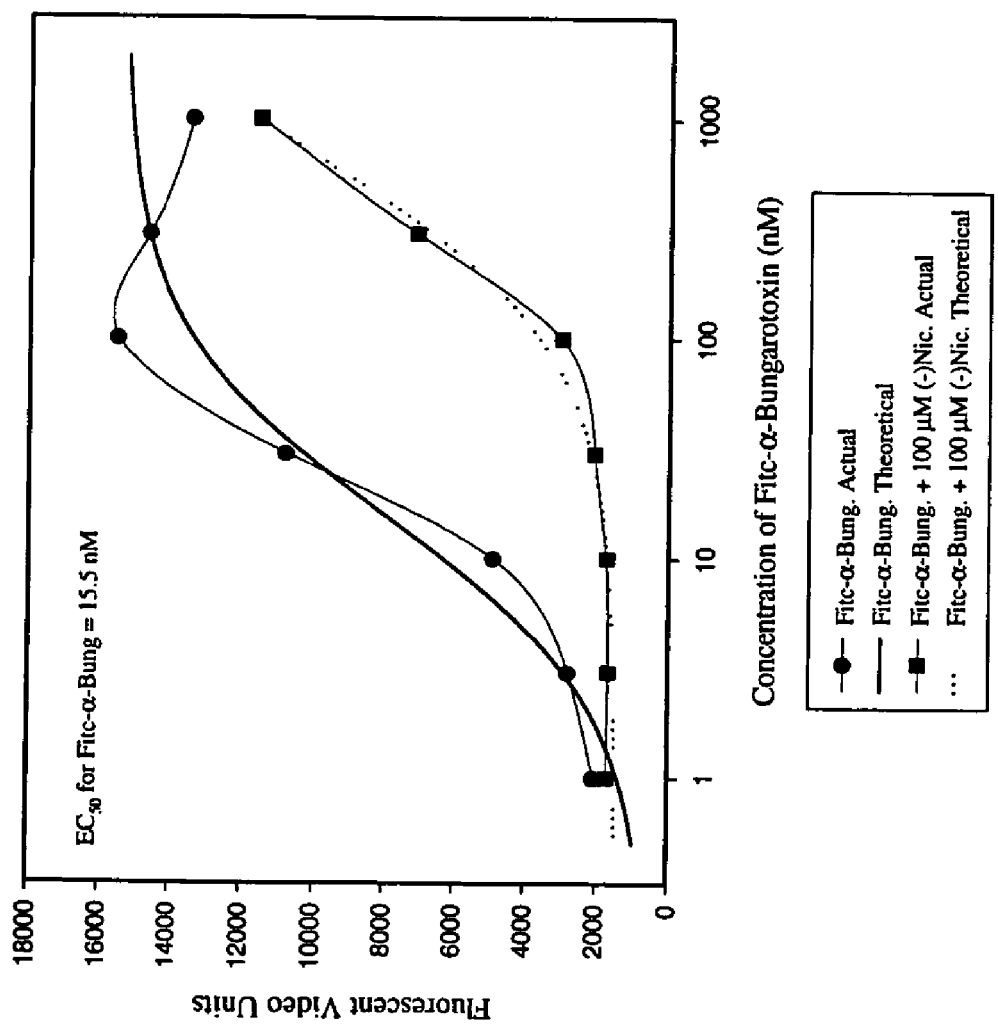
FIG. 3 Fl-btx binding to the α7/5-HT$_3$ Chimeric Ligand Gated Ion Channel

Sequence 1 DNA coding sequence of the wild type human α7 ligand gated ion channel
Sequence 2 Amino acid sequence of the wild type human α7 ligand gated ion channel
Sequence 3 DNA coding sequence of the murine 5HT$_3$ ligand gated ion channel
Sequence 4 Amino acid sequence of the murine 5HT$_3$ ligand gated ion channel
Sequence 5 DNA coding sequence of the human α7/murine 5HT$_3$ ligand gated ion channel
Sequence 6 Amino acid sequence of the human α7/murine 5HT$_3$ ligand gated ion channel
Sequence 7 GG443 PCR Primer
Sequence 8 GG444 PCR Primer
Sequence 9 DNA coding sequence of the mutant human α7 ligand gated ion channel containing the T→P mutation at amino acid position 230
Sequence 10 Amino acid sequence of the mutant human α7 ligand gated ion channel containing the T→P mutation at amino acid position 230
Sequence 11 DNA coding sequence of the mutant human α7 ligand gated ion channel containing the C→S mutation at amino acid position 241
Sequence 12 Amino acid sequence of the mutant human α7 ligand gated ion channel containing the C→S mutation at amino acid position 241
Sequence 13 DNA coding sequence of the double mutant human α7 ligand gated ion channel containing the T→P mutation at amino acid position 230 and the C→S mutation at amino acid position 241
Sequence 14 Amino acid sequence of the double mutant human α7 ligand gated ion channel containing the T→P mutation at amino acid position 230 and the C→S mutation at amino acid position 241

SUMMARY OF THE INVENTION

The present invention addresses the need identified above in that it provides methods and compositions useful for inducing inward conducting cation channels and cell lines expressing said channels to preferentially conduct calcium. Said inward cation channels can be either voltage gated ion channels, ligand gated channels, or non-voltage non-ligand gated ion channels.

In one embodiment, the invention includes a special cell culture medium comprising a high concentration of calcium and a relatively low concentration of sodium. The special cell culture medium comprises calcium ions at a concentration of from about 2 to 10 mM, sodium ions at a concentration of from about 0 to 50 mM, a pH between about 7.0–7.5, potassium between about 0.1–30 mM and a buffer compatible with mammalian cells. Because the ionic composition of the medium is reduced by the reduction in sodium ion content typically supplied by isotonic concentrations of sodium chloride the isotonicity of the media is retained by the addition of an impermeant cation in an amount sufficient to maintain isotonic conditions.

In another embodiment the invention includes methods of treating cells in aqueous culture medium, where the treatment comprises changing the aqueous environment of the cells from their beginning state, where they may exist in any aqueous buffered solution designed to maintain living cells, to a special cell culture medium where the ionic conditions comprise: calcium ions at a concentration of from about 2 to 10 mM, sodium ions from about 0 to 50 mM, pH from about 7.0 to 7.5 and impermeant cations in an amount sufficient to maintain isotonic conditions.

In another embodiment the invention includes methods of inducing cells that express either voltage gated, ligand gated or non-voltage non-ligand gated inward conducting cation channels to preferentially conduct calcium ions. This is known as calcium conductance or calcium flux, comprising: incubating the cells in a special cell culture medium described above for a length of time from between 15 minutes to about 8 hours. The conductance can then be measured in a variety of ways. A few of which are described.

In another particularly preferred embodiment the invention includes methods of inducing cells that express α7/5HT$_3$ chimeric receptors to preferentially conduct calcium ions comprising the step of incubating the cells in the above mentioned special cell culture media.

In another particularly preferred embodiment the invention includes methods of inducing cells that express a mutant α7 receptor to preferentially conduct calcium ions comprising the step of incubating the cells in the above mentioned special cell culture media.

In another embodiment the invention provides a chimeric α7/5-HT$_3$ nucleic acid molecule encoding a heretofore unknown chimeric ligand gated ion channel and constructs and recombinant host cells incorporating the isolated nucleic acid molecules; chimeric α7/5-HT$_3$ polypeptides encoded by the isolated nucleic acid molecule and methods of making and using all of the foregoing.

In yet another embodiment the invention provides heretofore unknown mutants of the human α7 nAChR ligand gated ion channel and constructs and recombinant host cells incorporating the isolated nucleic acid molecules; mutant α7 nAChR polypeptides encoded by the isolated nucleic acid molecules and methods of making and using all of the foregoing.

SEQ ID NOS: 5, 6, 9, 10, 11, 12, 13 and 14 provides particular human/mouse chimeric polynucleotide and polypeptide sequences and mutant α7 nAChR polynucleotide and polypetide sequences, and the invention is includes within its scope other human and mouse allelic variants and conservative amino acid substitutions. The polynucleotide sequences are intended to encompass the well known degeneracy of the genetic code.

In yet other embodiment the invention provides a fluorescent ligand binding assay comprising: incubating cells with a fluorescent ligand capable of binding to cell surface receptors and measuring the fluorescence of cell bound ligand using FLIPR. The invention also describes assays for selective agonists, antagonists and modulators of the α7 nAChR.

Additional Details of the Invention

There are many calcium influx assays suitable for high throughput screening but there are no good high throughput assays to measure the influx of other cations. Therefore it is desirable to induce a cell line that expresses inward conducting cation channels normally conducting other cations to preferentially conduct calcium. The present invention provides a methods and compositions of adapting an inward conducting cation channel to preferentially conduct calcium. Such inward conducting cation channels include voltage gated ion channels, ligand gated ionic channels, and non-voltage gated non-ligand gated ionic channels. Voltage gated ionic channels may be described as ion channels which open in response to a change in the voltage across the membrane. Ligand gated ion channels may be described as ion channels which open in response to the binding of a ligand to the channel protein. Non-voltage non-ligand gated ion channels may be described as channels which don not open in response to either voltage across the membrane or to ligand binding but that are regulated by covalent modifications by second messenger signaling pathways such as protein phosphorylation, or increases in channel gene expression leading to increases in ion channel density. Such a condition may exist, for example, in epithelial cells such as kidney epithelium cells and white blood cells.

As used herein the term "5HT-3 receptor" is used interchangeably with "5HT ligand gated ion channel" As used herein the term "α7 receptor" and "α7 nAChR" and "α7 ligand gated ion channel" are all used interchangeably. The term "mutant α7 receptors", "mutant α7 ligand gated ion channel" or mutant "α7 AchR" refers any one of a number of specific mutant polynucleotide or polypeptide species described herein. When a specific mutation is desired it referred to by the SEQ ID NO of its encoding nucleic acid, or by reference to the SEQ ID NO of the resultant predicted polypeptide product. By way of example, a cell line expressing a particular mutation might be referred to as cells expressing the polynucleotide sequence of SEQ ID NO: 13 or the polypeptide sequence of SEQ ID NO:14. As aid in understanding the reader is directed to the section entitled "Brief Description of the Sequence Listings"

Special Cell Culture Medium

The inventors provide an ionic environment that can be used with all of the ion channels described herein. The special cell culture medium provides a means of adapting ligand gated, voltage gated, and non-ligand gated non-voltage gated ion channels not normally conducting calcium to the conductance of calcium. The special cell culture medium provides a means of adapting those channels normally conducting sodium, potassium or other ions to the conductance of calcium whether those channels be of the ligand gated, voltagen gated, or non-ligand non voltage gated variety.

The inventors have addressed the task of inducing calcium flux or calcium conductance or transmission of calcium ions in ion channels not normally preferentially transmitting calcium ions by providing special cell culture compositions comprising a high concentration of calcium and a relatively low concentration of sodium. The special cell culture medium comprises calcium ions at a concentration of from about 2 to 10 mM, sodium ions at a concentration of from about 0 to 50 mM, a pH between about 7.0–7.5, potassium between about 0.1–30 mM and a buffer compatible with mammalian cells. It is understood by one of skill in the art that a variety of salts may be used as a source of sodium ions including but not limited by the examples of NaCl, Na2HPO4, NaH2PO4 and NaHCO3. It is understood by one of skill in the art that a variety of salts may be used as a source of potassium ions including but not limited by the examples of KCl, K2HPO4, KH2PO4 and KHCO3. It is understood by one of skill in the art that calcium ions may be supplied by a variety of salts including but not limited by the examples of CaCl2 and CaSO4. In addition all of the above ions may be supplied by salts of organic compounds within the knowledge of one of skill in the art.

Because the ionic composition of the medium is reduced by the reduction in sodium ion content typically supplied by isotonic concentrations of sodium chloride the isotonicity of the media is retained by the addition of an impermeant cation in an amount sufficient to maintain isotonic conditions. In the context of the present invention, the term "isotonic" means having an osmolality that is within the range tolerated by the cell or a solution that has the same osmotic pressure as the interior of the cell. Usually this is in the range of about 285–315 mOsm/kg H2O depending on the cell type and source, more preferably about 290–305, for most cell types this is about 300 mOsm/kg H2O.

Impermeant cations are defined as organic cations too large to pass through the channel of interest. By way of example only, such cations may include N-methyl-D-glucamine, choline, tetraethylammonium (TEA), tetrethymethyammonium (TMA) and tetrapropylammonium (TPA) and Tris.

In one particular embodiment, the cell culture medium comprises CaCl$_2$ at about 4 mM, MgSO$_4$ at about 0.8 mM, HEPES Buffer at about 20 mM, Glucose at about 6 mM, NaCl at about 20 mM, KCl at about 5 mM and the impermeant cation N-methyl-D-glucamine at about 120 mM.

It is understood by one skilled in the art that calcium flux or the transmission of calcium ions may be accessed by a number of well know methods. These include but are not limited by the measurement of voltage changes either directly or indirectly caused by the movement of calcium ions ie. measuring ionic flux or conductance. In addition the presence of calcium may be accessed by its interaction with a number of flourescent dyes well known in the art. These include but are not limited by the choices of Calcium Green and flou-3 and flou-4. It is understood that the fluorescent signal of the various dyes known in the art may be measured on FLIPR but also on other more conventional instrumentation including fluorimeters The present invention also provides a $\alpha7/5\text{-HT}_3$ chimeric receptor and a novel mutant human $\alpha7$ receptors encoded by isolated polynucleotides (e.g., DNA sequences and RNA transcripts, both sense and complementary antisense strands, both single and double-stranded, including splice variants thereof) encoding a human enzyme referred to herein as $\alpha7/5\text{-HT}_3$ chimera or mutant $\alpha7$ receptor DNA. Polynucleotides of the invention include cDNA, and DNA that has been chemically synthesized in whole or in part. "Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. "Isolated" as used herein and as understood in the art, whether referring to "isolated" polynucleotides or polypeptides, is taken to mean that it is uniquely created by the inventors, separated from the original cellular or genetic environment in which the polypeptide or nucleic acid is normally found. As used herein therefore, by way of example only, a transgenic animal or a recombinant cell line constructed with a polynucleotide of the invention, incorporates the "isolated" nucleic acid.

Allelic variants are modified forms of a wild type gene sequence, the modification resulting from recombination during chromosomal segregation or exposure to conditions which give rise to genetic mutation. Allelic variants, like wild type genes, are naturally occurring sequences (as opposed to non-naturally occurring variants which arise from in vitro manipulation).

A DNA sequence encoding a $\alpha7/5\text{-HT}_3$ polypeptide is set out in SEQ ID NO: 5. DNA sequences encoding the mutant $\alpha7$ receptor polypeptides are set out in SEQ ID NO: 9, 11 and 13. One of skill in the art will readily appreciate that the preferred DNA of the invention comprises a double stranded molecule, for example the molecule having the sequence set forth in SEQ ID NO: 5, 9, 11 or 13 along with the complementary molecule (the "non-coding strand" or "complement") having a sequence deducible from the sequence of SEQ ID NO: 5, 9, 11, or 13 according to Watson-Crick base pairing rules for DNA. Also preferred are other polynucleotides encoding the $\alpha7/5\text{-HT}_3$ polypeptides or mutant polypeptides of SEQ ID NO: 6, 10, 12, or 14 which differ in sequence from the polynucleotides of SEQ ID NO: 5, 9, 11 or 13 by virtue of the well known degeneracy of the genetic code.

The polynucleotide sequence information provided by the invention makes possible large-scale expression of the encoded polypeptide by techniques well known and routinely practiced in the art.

Autonomously replicating recombinant expression constructs such as plasmid and viral DNA vectors incorporating polynucleotides of the invention are also provided. Expression constructs wherein $\alpha7/5\text{-HT}_3$ chimera receptor or the novel mutant human $\alpha7$ receptor-encoding polynucleotides are operatively linked to an endogenous or exogenous expression control DNA sequence and a transcription terminator are also provided. Expression control DNA sequences include promoters, enhancers, and operators, and are generally selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but also may be utilized simply to amplify a $\alpha7/5\text{-HT}_3$ chimera receptor or the novel mutant human $\alpha7$ receptor-encoding polynucleotide sequence.

According to another aspect of the invention, host cells are provided, including prokaryotic and eukaryotic cells, comprising a polynucleotide of the invention (or vector of the invention) in a manner which permits expression of the encoded $\alpha7/5\text{-HT}_3$ chimera receptor or the novel mutant human $\alpha7$ receptor polypeptide. Polynucleotides of the invention may be introduced into the host cell as part of a circular plasmid, or as linear DNA comprising an isolated protein coding region or a viral vector. Methods for introducing DNA into the host cell well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, and mammalian cells systems.

Host cells for expression of $\alpha7/5\text{-HT}_3$ chimera receptor or the novel mutant human $\alpha7$ receptor polypeptides include prokaryotes, yeast, and higher eukaryotic cells. Suitable prokaryotic hosts to be used for the expression of $\alpha7/5\text{-HT}_3$ chimera receptor and or a mutant $\alpha7$ receptors include but are not limited to bacteria of the genera *Escherichia, Bacillus,* and *Salmonella,* as well as members of the genera *Pseudomonas, Streptomyces,* and *Staphylococcus.*

The isolated nucleic acid molecules of the invention are preferably cloned into a vector designed for expression in eukaryotic cells, rather than into a vector designed for expression in prokaryotic cells. Eukaryotic cells are preferred for expression of genes obtained from higher eukaryotes because the signals for synthesis, processing, and secretion of these proteins are usually recognized, whereas this is often not true for prokaryotic hosts (Ausubel, et al., ed., in Short Protocols in Molecular Biology, 2nd edition, John Wiley & Sons, publishers, pg. 16–49, 1992.). Eukaryotic hosts may include, but are not limited to, the following: insect cells, African green monkey kidney cells (COS cells), Chinese hamster ovary cells (CHO cells), human 293 cells, human SH-EP1 cells and murine 3T3 fibroblasts.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

The α7/5-HT$_3$ chimera receptor and the novel mutant human α7 receptor may also be expressed in yeast host cells from genera including *Saccharomyces, Pichia*, and *Kluveromyces*. Preferred yeast hosts are *S. cerevisiae* and *P. pastoris*. Yeast vectors will often contain an origin of replication sequence from a 2 micron yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*.

Insect host cell culture systems may also be used for the expression of human α7/5-HT$_3$ chimera receptor or the novel mutant human α7 receptor II polypeptides. In a preferred embodiment, the α7/5-HT$_3$ chimera receptor and the novel mutant human α7 receptor II polypeptides of the invention are expressed using a baculovirus expression system. Further information regarding the use of baculovirus systems for the expression of heterologous proteins in insect cells are reviewed by Luckow and Summers, *Bio/Technology* 6:47 (1988).

In another preferred embodiment, the α7/5-HT$_3$ chimera receptor or the novel mutant human α7 receptor II polypeptide is expressed in mammalian host cells. Non-limiting examples of suitable mammalian cell lines include the COS-7 line of monkey kidney cells (Gluzman et al., *Cell* 23:175 (1981)), Chinese hamster ovary (CHO) cells, and human 293 cells.

The choice of a suitable expression vector for expression of the human α7/5-HT$_3$ chimera receptor or the novel mutant human α7 receptor II polypeptid of the invention will of course depend upon the specific host cell to be used, and is within the skill of the ordinary artisan. Examples of suitable expression vectors include pcDNA3 (Invitrogen) and pSVL (Pharmacia Biotech). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

The invention also provides α7/5-HT$_3$ chimera receptor or novel mutant human α7 receptor II polypeptides encoded by a polynucleotides of the invention. Presently preferred is α7/5-HT$_3$ chimera polypeptide comprising the amino acid sequence set out in SEQ ID NO: 6 and a novel mutant human α7 receptor comprising the amino acid sequence set out in SEQ ID NO: 14

Polypeptides of the invention may be produced natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated form of α7/5-HT$_3$ chimera receptor or the novel mutant human α7 receptor II are embraced.

The invention also embraces variant α7/5-HT$_3$ chimera receptor or the novel mutant human α7 receptor polypeptides wherein the essential activity, including pharmacology which accurately mimics that of the native α7 ligand gated ion channel receptor of the α7/5-HT$_3$ chimera receptor or the novel mutant human α7 receptor II is maintained. Examples of such variants include insertion, deletions or substitutions. Insertional variants also include fusion proteins wherein the amino and/or carboxy termini of the α7/5-HT$_3$ chimera receptor or the novel mutant human α7 receptor is fused to another polypeptide. It is further envisioned that the although the polypeptides of the invention are disclosed as mature protein sequences in SEQ ID NOS: 6, 10, 12, and 14, which include a signal sequence necessary for insertion into the cell membrane, the invention also includes polypeptides with the signal sequence removed. FIG. 2 provides a sequence representing indicating that the mature protein of α7 AChR derived polypeptides including the mutant polypeptides and the chimeric polypeptide have 22 amino acids removed in the mature form.

In another aspect, the invention provides deletion variants wherein one or more amino acid residues in a α7/5-HT$_3$ chimera receptor or the novel mutant human α7 receptor polypeptide are removed. Deletions can be effected at one or both termini of the α7/5-HT$_3$ chimera receptor or the novel mutant human α7 receptor polypeptide, or with removal of one or more residues within the α7/5-HT$_3$ chimera receptor or the novel mutant human α7 receptor amino acid sequence.

In still another aspect, the invention provides substitution variants of α7/5-HT$_3$ chimera receptor and the novel mutant human α7 receptor polypeptides. Substitution variants include those polypeptides wherein one or more amino acid residues of a α7/5-HT$_3$ chimera receptor and the novel mutant human α7 receptor polypeptide are removed and replaced with alternative residues. In one aspect, the substitutions are conservative in nature, however, the invention embraces substitutions that are also non-conservative. Conservative substitutions for this purpose may be defined as set out in Tables A, B, or C below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below.

TABLE A

Conservative Substitutions I

| SIDE CHAIN CHARACTERISTIC | AMINO ACID |
|---|---|
| Aliphatic | |
| Non-polar | G A P |
| | I L V |
| Polar-uncharged | C S T M |
| | N Q |

TABLE A-continued

Conservative Substitutions I

| SIDE CHAIN CHARACTERISTIC | AMINO ACID |
|---|---|
| Polar-charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:N.Y. (1975), pp. 71–77] as set out in Table B, immediately below

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

EXAMPLE 1

Construction of Chimeric α7/5-HT$_3$ Receptor

PCR Primers GG443 (SEQ ID NO:7) and GG444 SEQ ID NO:8 were used to isolate the DNA encoding the N-terminal 201 amino acids from the human α7 nAChR (FIG. 1).

GG443:
5' GGC<u>TCTAGA</u>CCACCATGCGCTGTTCACCGGGAGGCGTCTGGCTG 3'

GG444:
5' GGG<u>TGATCA</u>CTGTGAAGGTGACATCAGGGTAGGGCTC 3'

The isolated DNA fragment of encoding the N-terminus of the α7 was engineered to have an Xba 1 site at the 5'end and Bcl 1 site at the 3' end. The engineered restriction sites are underlined in each respective primer. The pore forming domain of the mouse 5-HT$_3$ cDNA was then isolated as a Bcl 1/Sal 1 DNA fragment of the complete mouse cDNA gene. A ligation reaction was used to join the 5' of the α7 cDNA with the 3' end of the 5-HT$_3$ cDNA. This ligated fragment was isolated and purified and then cloned into the Xba1 Sal 1 site of two mammalian expression plasmid vectors termed pGG764 and pGG759. The parental plasmid termed pGG764, which contained the G418 resistance gene also contained a cytomegalovirus (CMV) promoter and a bovine growth hormone polyadenylation site for the initiation and termination of mRNA transcription. The parental plasmid termed pGG759 contained the hygromycin resistance gene and the identical mRNA initiation and termination regulatory elements. The new plasmid derived from the insertion of α7/5-HT$_3$ gene into pGG764 was termed pGS 175. The new plasmid derived from the insertion of α7/5-HT$_3$ gene into pGG759 was termed pGS176. Both pGS175 and pGS179 were transformed into E. coli and isolated colonies were picked and expanded. The DNA from each plasmid was isolated and sequenced to verify that both constructions were correct. The sequence obtained for the coding region of the α7/5-HT$_3$ cDNA construct is shown in SEQ ID NO: 5 and the predicted amino acid sequence of the construct is given in in SEQ ID NO: 6

It is understood that once one skilled in the art has possession of applicant's chimeric α7/5-HT$_3$ and mutant α7 AChRs a number of novel assays are evident for the assessment of ligand binding, of the ability of test compounds to function as agonists, and to measure the ability of test compounds to function as modulators of α7 activity. Details are provided in the examples below. It is understood however that one skilled in the art might perform the same essential functions in a variety of way and the examples are in no way intended to indicate limitations in the claims.

Expression of the Chimeric Receptor

The α7/5-HT$_3$ cDNA inserted into pGS175 and pGS179 were simultaneously transfected into SH-EP1 cells using cationic lipid transfection reagent and cells expressing the α7/5-HT$_3$ channel were selected using 800 μg/ml geneticin (G418) and 400 μg/ml of hygromycin B. Cells expressing the chimeric protein at high levels were identified by measuring fluorescein-α-bungarotoxin binding (see FIG. 3). Isolated clones were grown in Eagle's minimal essential medium (MEM) supplemented with 10% fetal bovine serum (FBS), 4 mM L-Glutamine, Fungi-Bact.(1:100), 400 μg/ml hygromycin B, and 800 μg/ml G418. All cells were maintained in an incubator at 37° C. in a humidified 6% $CO_2$ atmosphere.

EXAMPLE 2

Fluorescein Labeled α-bungarotoxin (fl-btx) Binding Assay

The α7/5-HT$_3$-SHEP cells were grown in minimal essential medium (MEM) containing nonessential amino acids supplemented with 10% fetal bovine serum, L-glutamine, 100 units/ml penicillin/streptomycin, 250 ng/ml fungizone, 400 µg/ml Hygromycin-B, and 800 µg/ml Geneticin. The cells were grown in a 37° C. incubator with 6% $CO_2$. The α7/5-$HT_3$-SHEP cells were trypsinized and plated in 96 well plates with dark side walls and clear bottoms (Coming # 3614) at density of 2 6×10$^4$ cells per well two days before analysis. On the day of the analysis, the cells were wash four times using a Bio-Tek plate washer. After the fourth cycle, the final volume in each well was 100 µl. Cellular fluorescence was analyzed on FLIPR (Molecular Devices) after the addition of a 100 µl of a 2× stock fluorescein labeled α-bungarotoxin (F-1176 Molecular Probes: Fl-btx). In competition experiments the competing ligand was added as a 2× drug stock before the addition of Fl-btx. Fluorescence was measured by exciting the dye at 488 nm using 500 mW of power. A 0.5 second exposure was used to illuminate each well. Fluorescence emmission was recorded above 525 nm. Fluorescence was detected using a F-stop set of either 2.0 or 1.2. The cellular fluorescence was so intense that subsequent washing was not needed to measure cellular fluorescence.

Figure 4:
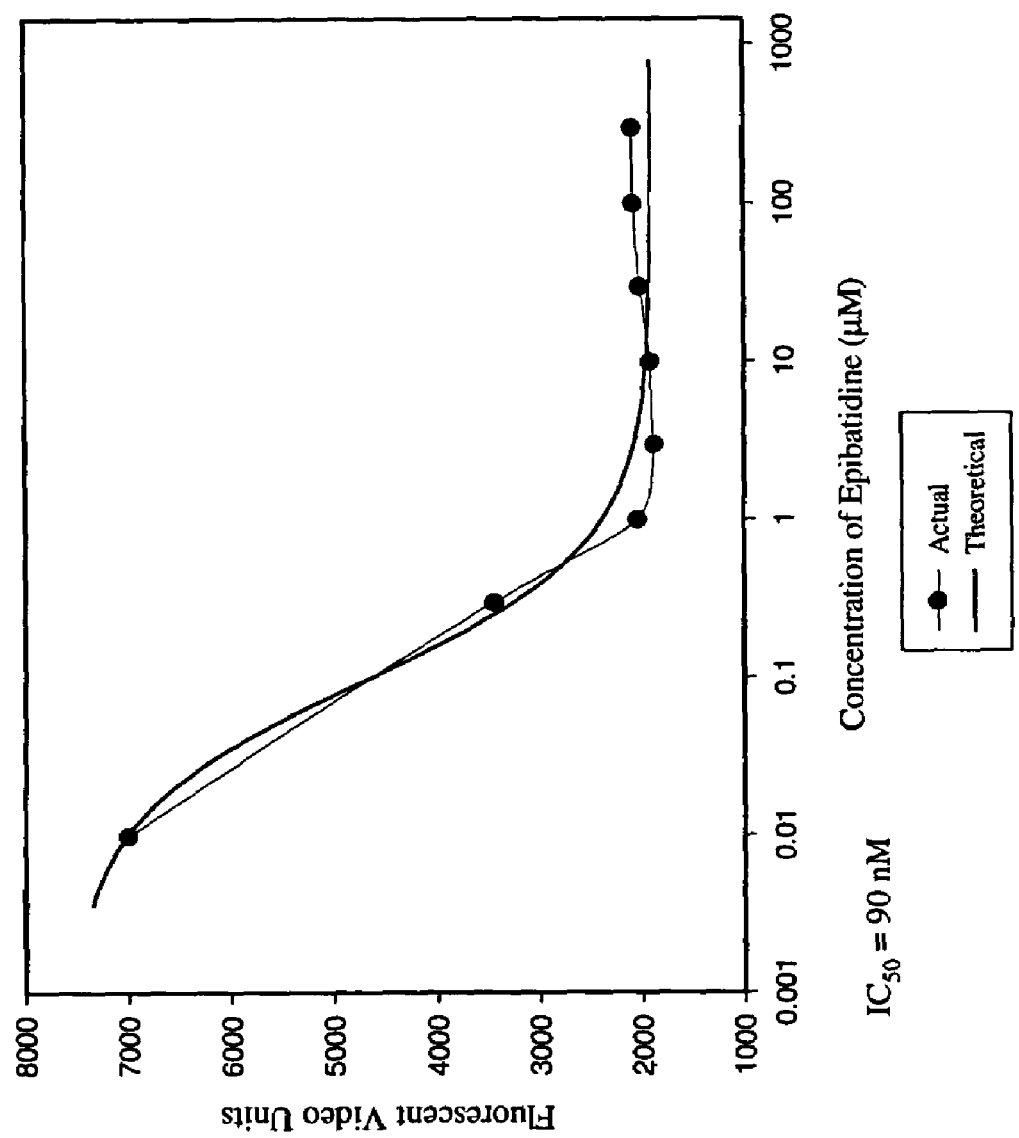
FIG. 4 Epibatidine Competes Fl-btx Binding to α7/5-HT$_3$ Chimeric Ligand Gated Ion Channel FIG. 5 α-btx Competes Fl-btx Binding to α7/5-HT$_3$ Chimeric Ligand Gated Ion Channel FIG. 6 Non-Physiologic Buffer Increases Calcium Flux through the α7/5-HT$_3$ Chimeric Ligand Gated Ion Channel FIG. 7 Non-Physiologic Buffer does not Increase the Bradykinin-Induced Calcium Flux FIG. 8 Exemplary Data from a screen for modulators of activity indicating a test compound is an antagonist FIG. 9 Assay of function of double mutant human α7 ligand gated ion channel FIG. 10 Exemplary Data from a screen for modulators of activity indicating a test compound is an antagonist
Figure 5:
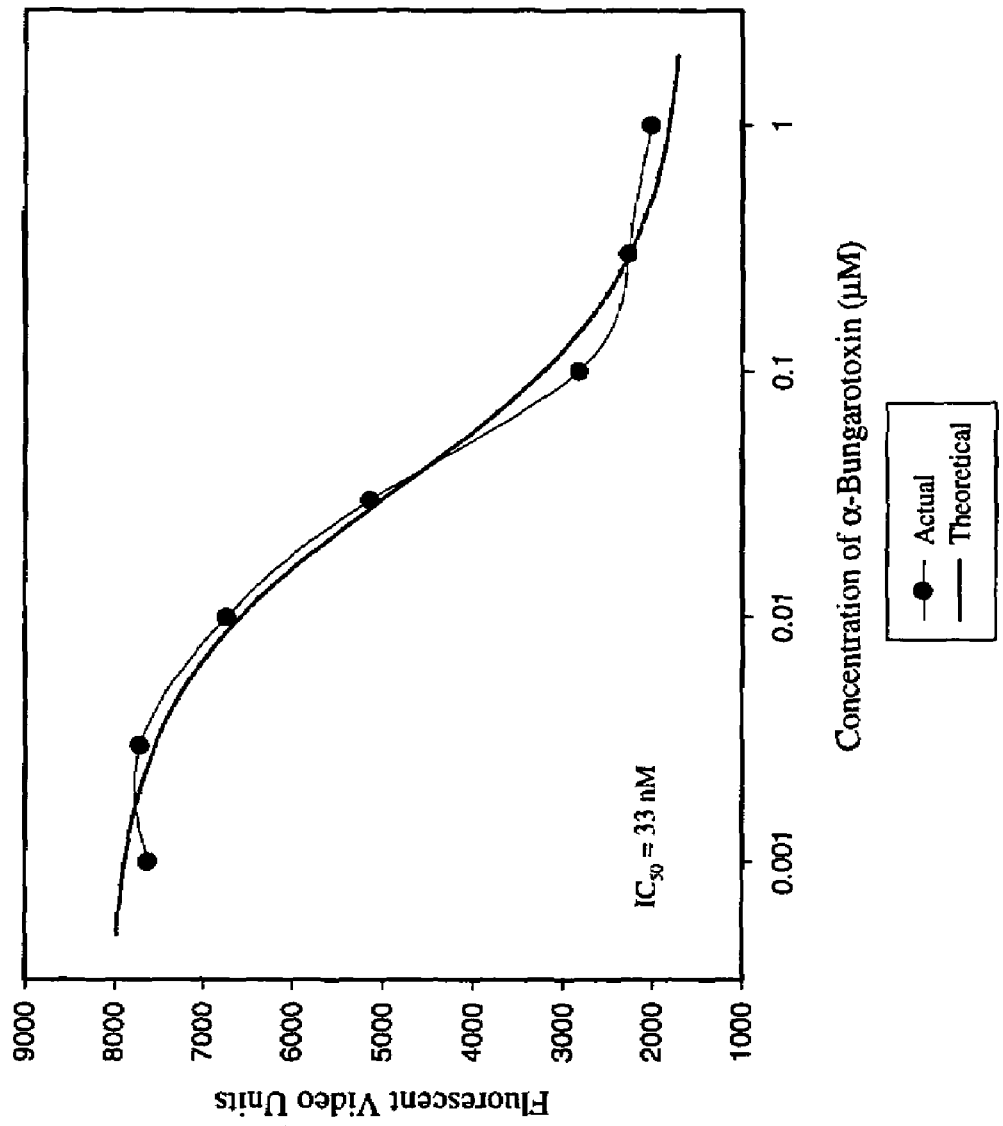

The data in FIG. 3 shows that Fl-btx binding is a saturable reaction with a Ki of 15.5 nM. Nicotine at 100 µM competes at all concentrations of Fl-btx (FIG. 3). FIGS. 4 and 5 show that epibatidine and unlabeled α-btx also compete for Fl-btx binding with a Ki of 90 nM and 33 nM respectively. The data in Table 1 provide a summary of the effect of seven structurally unrelated molecules in the whole cell Fl-btx binding assay.

| Agonists/Antagonists | Fitc-α-Bungoarotoxin Binding (30 nM) |
|---|---|
| (−) Nicotine | $IC_{50}$ = 9.7 µM |
| (+/−) Epibatidine | $IC_{50}$ = 90 nM |
| GTS-21 | $IC_{50}$ = 16 µM |
| ABT-418 | $IC_{50}$ = 38 µM |
| Anabasiene | $IC_{50}$ = ND |
| Mecamylamine | $IC_{50}$ = >300 µM |
| Methyllcaconitine (MLA) | $IC_{50}$ = 26 nM |

The rank order potency of these compounds follow the known pharmacology of α7 nAChR (Holliday et al 1997). Taken together these data show that the fl-btx binding assay on the α7/5-$HT_3$ chimera receptor can be used to novel and selective agonists and antagonists of endogenous α7 nAChR.

The whole cell binding assay described in this example is useful in many regards not the least of which is that α7 nAChR is in its native configuration, only cell surface α7 nAChR is a binding target, the assay is simpler because there is no need to prepare membranes, and there are no radioisotopes being used and because fluorescence is detected within approximately 200 microns of the bottoms of the wells the need for extensive washing is eliminated.

Our results as summarized in the Figures demonstrate that the α7/5-$HT_3$ SH-EP cell line can be used in the Fl-btx binding assay on FLIPR. The pharmacology of the α7/5-$HT_3$ receptor suggests that the Fl-btx binding assay can be used in a HTS format to find novel α7 nAChR agonists and antagonists.

EXAMPLE 3

Calcium Flux Assay—Identification of an α7 nAChR Agonist

The α7/5-$HT_3$-SHEP or alternatively the human α7 nACHR double mutant SHEP (described below) cells were grown in minimal essential medium (MEM) containing nonessential amino acids supplemented with 10% fetal bovine serum, L-glutamine, 100 units/ml penicillin/streptomycin, 250 ng/ml fungizone, 400 µg/ml Hygromycin-B, and 800 µg/ml Geneticin. The cells were grown in a 37° C. incubator with 6% $CO_2$. The α7/5-$HT_3$-SHEP cells were trypsinized and plated in 96 well plates with dark side walls and clear bottoms (Corning # 3614) at density of 2 6×10$^4$ cells per well two days before analysis. The cells were loaded in a 1:1 mixture of 2 mM Calcium Green-1, AM (Molecular Probes) prepared in anhydrous dimethylsulfoxide and 20% pluonic F-127 (Molecular Probes). This reagent was added directly to the growth medium of each well to achieve a final concentration of 2 µM of Calcium Green-1, AM. The cells were incubated in the dye for one hour at 37° C. and then washed with 4 cycles of Bio-Tek plate washer. Each cycle was programmed to wash each well with four times with either EBSS or MMEBSS. After the third cycle, the cells were allowed to incubate at 37° C. for at least ten minutes. After the fourth cycle final volume in each well was 100 µl. The cells were analyzed on FLIPR (Molecular Devices) for the change in fluorescence after the addition of a 100 µl of a 2× drug stock. FLIPR was set up to excite the dye with at 488 nanometers using 500 mW of power. A 0.5 second exposure was used to illuminate each well. Fluorescence emission was recorded above 525 nm. Fluorescence was detected using a F-stop set of either 2.0 or 1.2.

Under physiological ionic conditions, the 5-$HT_3$ ligand gated ion channel conducts primarily $Na^+$ and is a poor conductor of $Ca^{++}$(Yang 1990; Brown et al 1998). Whereas, under physiological ionic conditions the α7 nACh channel conducts primarily $Ca^{++}$.

Figure 6:
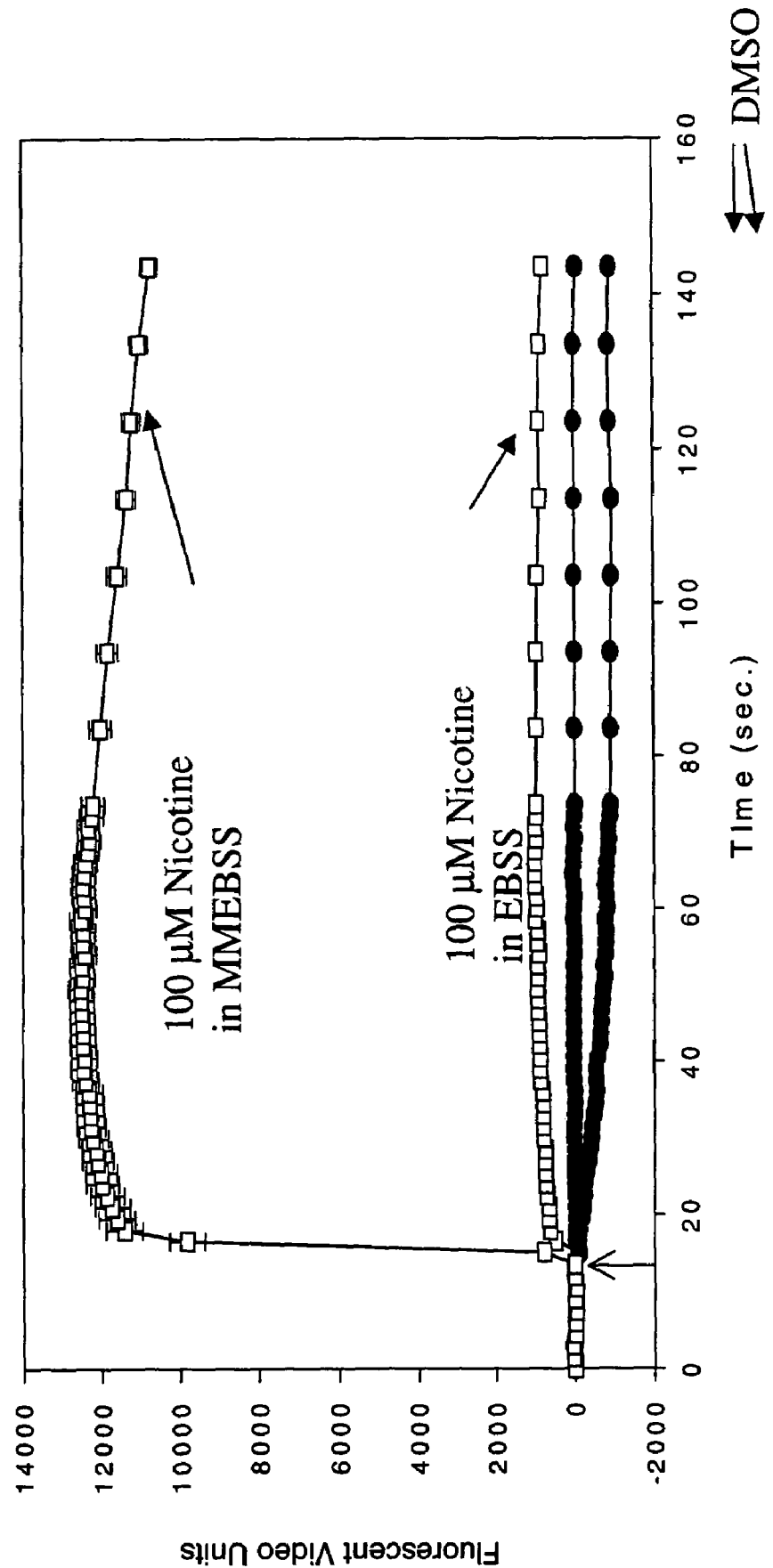
Figure 7:
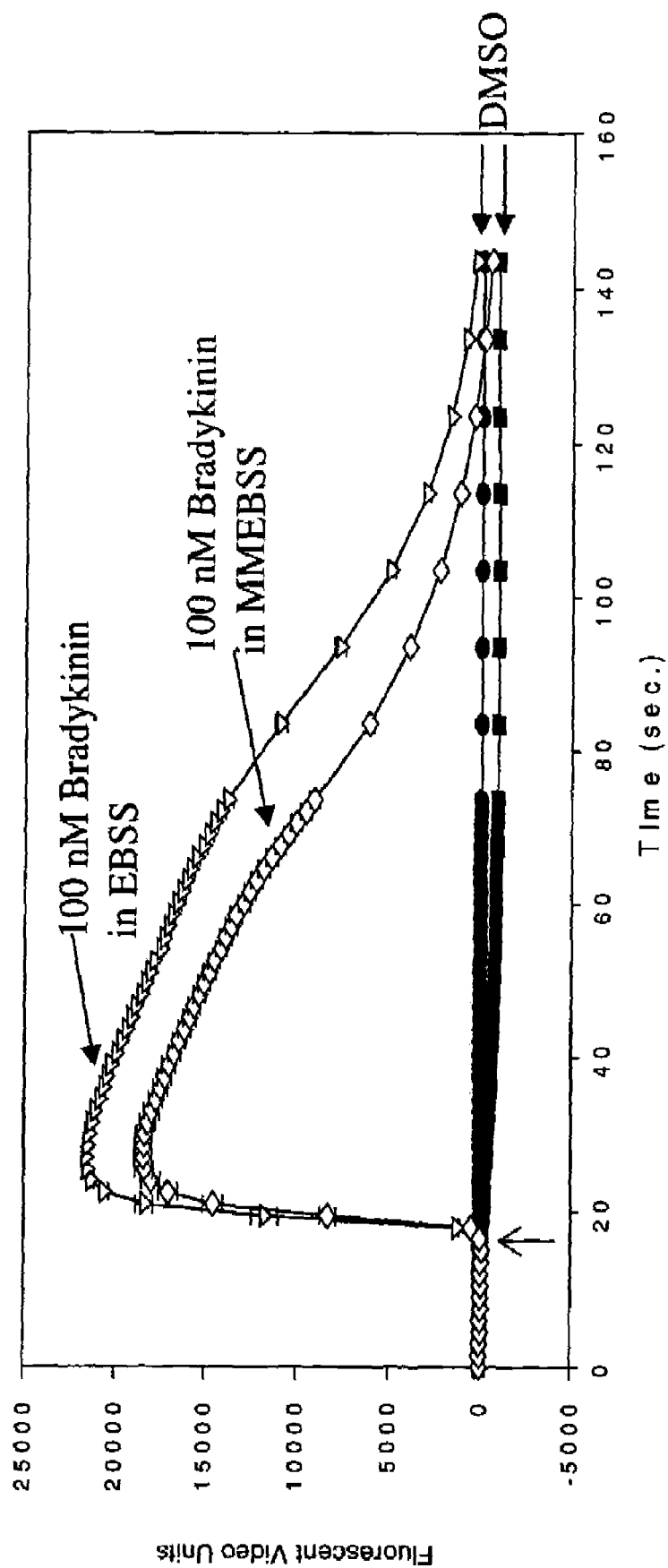

Therefore a particular embodiment of a special cell culture media, designated MMEBSS was used to enhance the agonist-evoked flux of calcium through the α7/5-$HT_3$ channel expressed in SH-EP1 cells (FIG. 6). We compared the physiological Earles Balanced Salt Solution (EBBS) buffer and the special cell culture media (MMEBSS) in the $Ca^{++}$ functional assay on FLIPR. The result of this experiment clearly indicated that under physiological conditions (EBBS) little calcium was detected in response to a maximally effective concentration of (−) nicotine (100 µM). Other the other hand using the special cell culture media, (MMEBSS) 100 µM (−) nicotine evoked a large increase in intracellular calcium (FIG. 6). Under these conditions, FLIPR can be used to accurately measure agonist activity of the α7/5-$HT_3$ channel (Table 2). The α7/5-$HT_3$-SH-EP1 cells express an endogenous bradykinin receptor that when stimulated with 100 nM bradykinin produces a maximal increase in intracellular calcium by releasing calcium from intracellular stores. The data in FIG. 7 show that the bradykinin-induced calcium flux was similar in EBSS and MMEBSS. These data indicate that the effect of MMEBSS was specific for the calcium flux through the α7/5-HT3 channel The special cell culture media, designated MMEBSS is comprised of 4 mM $CaCl_2$, 0.8 mM $MgSO_4$, 20 mM NaCl, 5.3 mM KCL, 5.6 mM D-Glucose, 120 mM N-Methyl-D-Glucosamine, 9 mM Tris base and 20 mM HEPES. A detailed description of the preparation of MMEBSS is provided below. It should be recognized however that the recipe below is provided by way of example only and that the applicants intends to claim the full range of what they have invented.

| MMEBSS Buffer | | | |
|---|---|---|---|
| Buffer Component | Stock Solution | 2 Liters | Final Concentration |
| CaCl$_2$ Dihydrate | 1M | 10 ml. | 4 mM |
| MgSO$_4$ 7H$_2$O | 1M | 1.6 ml. | 0.8 mM |
| NaCl | 2M | 20 ml. | 20 mM |
| KCl | | 0.8 gr. | 5.3 mM |
| D-Glucose | | 2.0 gr. | 5.6 mM |
| Tris-HEPES[1] | 1M | 40 ml. | 20 mM |
| N-Methyl-D-Glucamine (pH 7.3)[2] | 1.36 | 176.5 ml | 120 mM |
| Tris Base[3] | | 0.5 gr | |

[1] 1M. Tris-HEPES pH 7.4 is formulated by weighing 47.66 grams of HEPES and adding approximately 8 of Tris base in 150 ml of water, the pH is adjusted to 7.4 with HCl. The final volume is adjusted to 200 ml.
[2] 1.36 M. N-Methyl-D-Glucamine/HCl pH 7.3 is formulated by adding 265.47 grams of N-Methyl-D-Glucamine in 500 ml. water 115 ml concentrated HCl is then added to the solution with stirring. The final pH is adjusted to 7.4
[3] Final concentration of Tris in buffer is approximately 9 mM For the experiments described above the physiologic buffer designated Earles Balanced Salt Solution was also prepared or purchased.

The compositions of EBSS and MMEBSS are compared below.

| Earle's Balanced Salt Solution (EBSS) | |
|---|---|
| CaCl$_2$ | 1.8 mM |
| MgSO$_4$ | 0.8 mM |
| NaHPO$_4$ | 1.0 mM |
| NaHCO$_3$ | 26 mM |
| Hepes | 20 mM |
| Glucose | 5.6 mM |
| NaCl | 117.0 mM |
| KCl | 5.3 mM |

| MMEBSS | |
|---|---|
| CaCl$_2$ | 4.0 mM |
| MgSO$_4$ | 0.8 mM |
| NaHPO$_4$ | 0.0 mM |
| NaHCO$_3$ | 0.0 mM |
| Hepes | 20 mM |
| Glucose | 5.6 mM |
| NaCl | 20.0 mM |
| KCl | 5.3 mM |
| N-methyl-D-glucamine | 120 mM also includes Tris base |

The summary of the pharmacological results using the α7/5-HT$_3$ channel as a drug target is listed in Table 2.

| Characterization of the α7/5-HT$_3$ Chimeric Channel | | |
|---|---|---|
| | α7/5-HT$_3$ EC$_{50}$ (μM)* | α7 nAChR EC$_{50}$ (μM)* |
| Nicotine | 5.7 | 10–50 |
| Epibatidine | 0.120 | 2 |
| ABT | 27 | 70 |
| Anabaseine | 6.6 | 6 |
| GTS-21 | 30 | 30 |

*"EC$_{50}$" is the effective concentration that produces a 50% maximal response.

These data establish that agonist activity of the α7/5-HT$_3$ channel can be used to predict the agonist activity at the endogenous α7 nACh receptor and thus provide evidence that the α 7/5-HT$_3$ channel can be use as a drug target to find novel α 7 nAChR agonists.

EXAMPLE 4

Calcium Flux Assay—Identification of an α7 nAChR Antagonist

Figure 8:
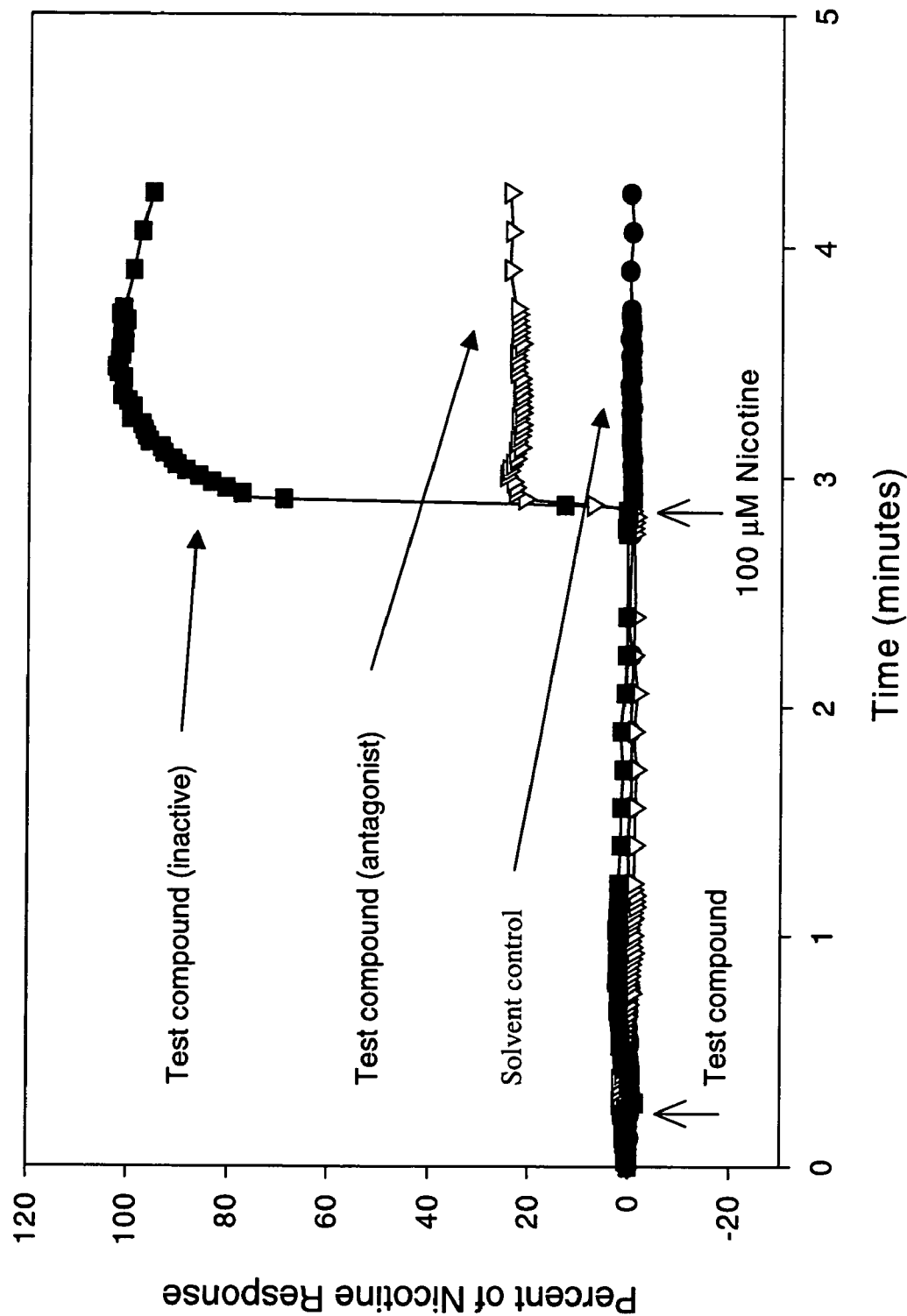

The SH-EP1 cells expressing the 7/5-HT$_3$ nAChR (7/5-HT$_3$-SHEP) or alternatively the human α7 nAChR double mutant SHEP cells(described below) were grown in minimal essential medium (MEM) containing nonessential amino acids supplemented with 10% fetal bovine serum, L-glutamine, 100 units/ml penicillin/streptomycin, 250 ng/ml fungizone, 400 ug/ml Hygromycin-B, and 800 ug/ml Geneticin. The cells were grown in a 37° C. incubator with 6% CO$_2$. The 7/5-HT$_3$-SHEP cells were trypsinized and plated in 96 well plates with dark side walls and clear bottoms (Corning # 3614) at density of 2 6×10$^4$ cells per well two days before analysis. The 7/5-HT$_3$-SHEP cells were loaded in a 1:1 mixture of 2 mM Calcium Green-1, AM (Molecular Probes) prepared in anhydrous dimethylsulfoxide and 20% pluonic F-127 (Molecular Probes). This reagent was added directly to the growth medium of each well to achieve a final concentration of 2 M of Calcium Green-1, AM. The α7/5-HT$_3$-SHEP cells were incubated in the dye for one hour at 37° C. and then washed with 4 cycles of Bio-Tek plate washer. Each cycle was programmed to wash each well with four times with either EBSS or MMEBSS. After the third cycle, the α7/5-HT$_3$-SHEP cells were allowed to incubate at 37° C. for at least ten minutes. After the fourth cycle final volume in each well was 100 l. Antagonist activity was measured as a decrease in nicotine-induced calcium influx using α7/5-HT$_3$ channel as a drug target. FLIPR (Molecular Devices) was set up to measure intracellular calcium by exciting the Calcium Green with at 488 nanometer using 500 mW of power and reading fluorescence emission above 525 nanometers. A 0.5 second exposure was used to illuminate each well. Fluorescence was detected using a F-stop set of either 2.0 or 1.2. Specifically, after 30 seconds of baseline recording, test compounds were added to each well of a 96 well plate using 50 ul from a 3× drug stock. 180 seconds after the addition of the test compounds, nicotine was added to each well to achieve a final concentration of u 100 M. In each experiment, 4 wells were used as solvent controls. As indicated in FIG. 8 antagonist activity was measured as a decrease in the 100 M nicotine-induced calcium influx relative to the effect of u 100 M nicotine in the solvent control wells.

EXAMPLE 5

Construction of the Human α7 Mutant Receptors

We discovered that it was possible by introducing certain non-conservative amino acid changes at the amino acid positions corresponding to positions 230 and 241 of the human sequence to recreate the desireable properties of the human/mouse α7nAChR/5-HT$_3$ hybrid. The two primer system utilized in the Transformer Site-Directed Mutagenesis kit from Clontech (LaJolla Calif.), may be employed for introducing site-directed mutants into the human α7 sequence of SEQ ID NO: 1 Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

A mutant α7 is prepared using Transformer TM site-directed mutagenesis kit, according to the manufacturer's protocol roughly outlined above. In one mutant, a codon in the channel mRNA is changed from ACG to CCG with the A at position 688 being changed to a C thus creating a mutant channel with threonine changed to proline at amino acid position number 230. The polynucleotide and predicted amino acid sequence of the entire mutant α7 ligand gated ion channel containing the T→P mutation is set forth in SEQ ID NO: 9 and 10 respectively. In another mutant, a codon in the channel mRNA is changed from TGT to AGT with the T at position 721 being changed to A thus creating a mutant channel with cysteine changed to serine at amino acid position 241. The polynucleotide and predicted amino acid sequence of the entire mutant α7 ligand gated ion channel containing the C→S mutation is set forth in SEQ ID NO: 11 and 12 respectively. In another mutant, both of the above mentioned mutations are introduced into the same DNA construct encoding a channel mRNA. The polynucleotide and predicted amino acid sequence of the double mutant α7 ligand gated ion channel containing the T→P mutation and the C→S mutation is set forth in SEQ ID NO: 13 and 14 respectively.

This double mutant channel protein has been shown to exhibit the desirable characteristics of the chimeric α7/5-HT$_3$ ligand gated ion channel including stability and assay characteristics when expressed in human SH-EP1 cells. Exemplary expression methods are described elsewhere and are fully within the ordinary skill of one in the art.

EXAMPLE 6

Functional Results with Double Mutant

Figure 9:
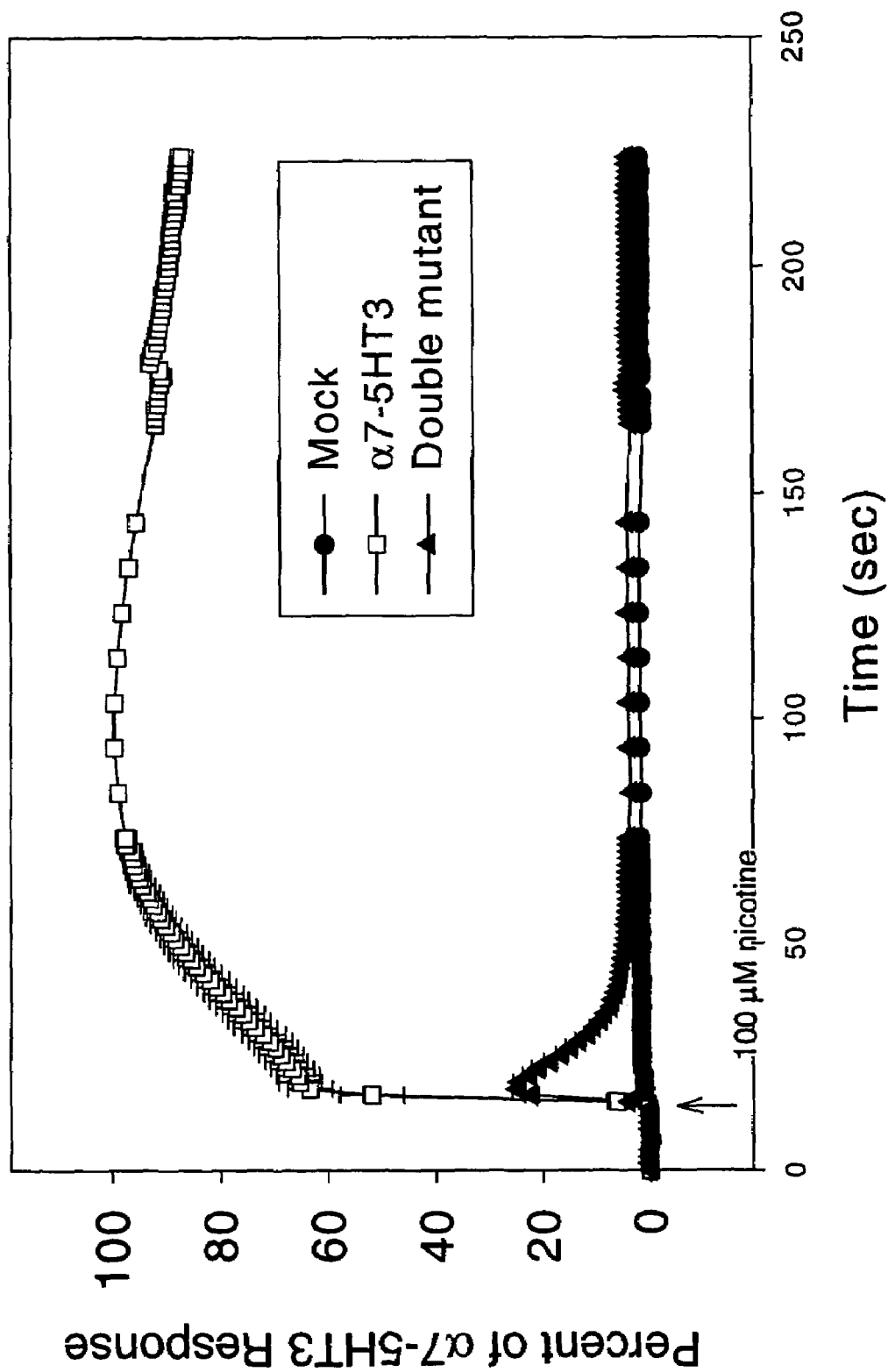

The SH-EP1 cells expressing the double mutation of SEQ ID NO:13 (double mutant SHEP cells )are grown in minimal essential medium (MEM) containing nonessential amino acids supplemented with 10% fetal bovine serum, L-glutamine, 100 units/ml penicillin/streptomycin, 250 ng/ml fungizone, 400 ug/ml Hygromycin-B, and 800 ug/ml Geneticin. The cells are grown in a 37° C. incubator with 6% $CO_2$. The 7-double mutant SHEP cells were trypsinized and plated in 96 well plates with dark side walls and clear bottoms (Corning # 3614) at density of 2 6×10$^4$ cells per well two days before analysis. The double mutant-SHEP cells are loaded in a 1:1 mixture of 2 mM Calcium Green-1, AM (Molecular Probes) prepared in anhydrous dimethylsulfoxide and 20% pluonic F-127 (Molecular Probes). This reagent was added directly to the growth medium of each well to achieve a final concentration of 2 M of Calcium Green-1, AM. The double mutant SHEP cells were incubated in the dye for one hour at 37° C. and then washed with 4 cycles of Bio-Tek plate washer. Each cycle was programmed to wash each well with four times with either EBSS or MMEBSS. After the third cycle, the double mutant-SHEP cells were allowed to incubate at 37° C. for at least ten minutes. After the fourth cycle final volume in each well was 100 l. Expression of the mutant α7 receptor was analyzed by measuring agonist-induced changes in intracellular calcium accumulation. FLIPR (Molecular Devices) was set up to excite Calcium Green with at 488 nanometer using 500 mW of power and reading fluorescence emission above 525 nanometers. A 0.5 second exposure was used to illuminate each well. Fluorescence was detected using a F-stop set of either 2.0 or 1.2. Specifically, after 30 seconds of baseline recording, test compounds were added to each well of a 96 sell plate using a 100 l from a 2× drug stock. In each experiment, at least 4 wells contained 7/5-HT$_3$-SHEP cells as positive controls. As indicated in FIG. 9 agonist activity was measured as an increase in intracellular calcium over baseline. As indicated in FIG. 9 this paradigm identified clonal cell lines that functionally expressed the double mutant α7 receptor. All attempts to express the wild type 7 nAChR using similar methods were totally unsuccessful.

EXAMPLE 7

Calcium Flux Assay: Modulator Screen

Figure 10:
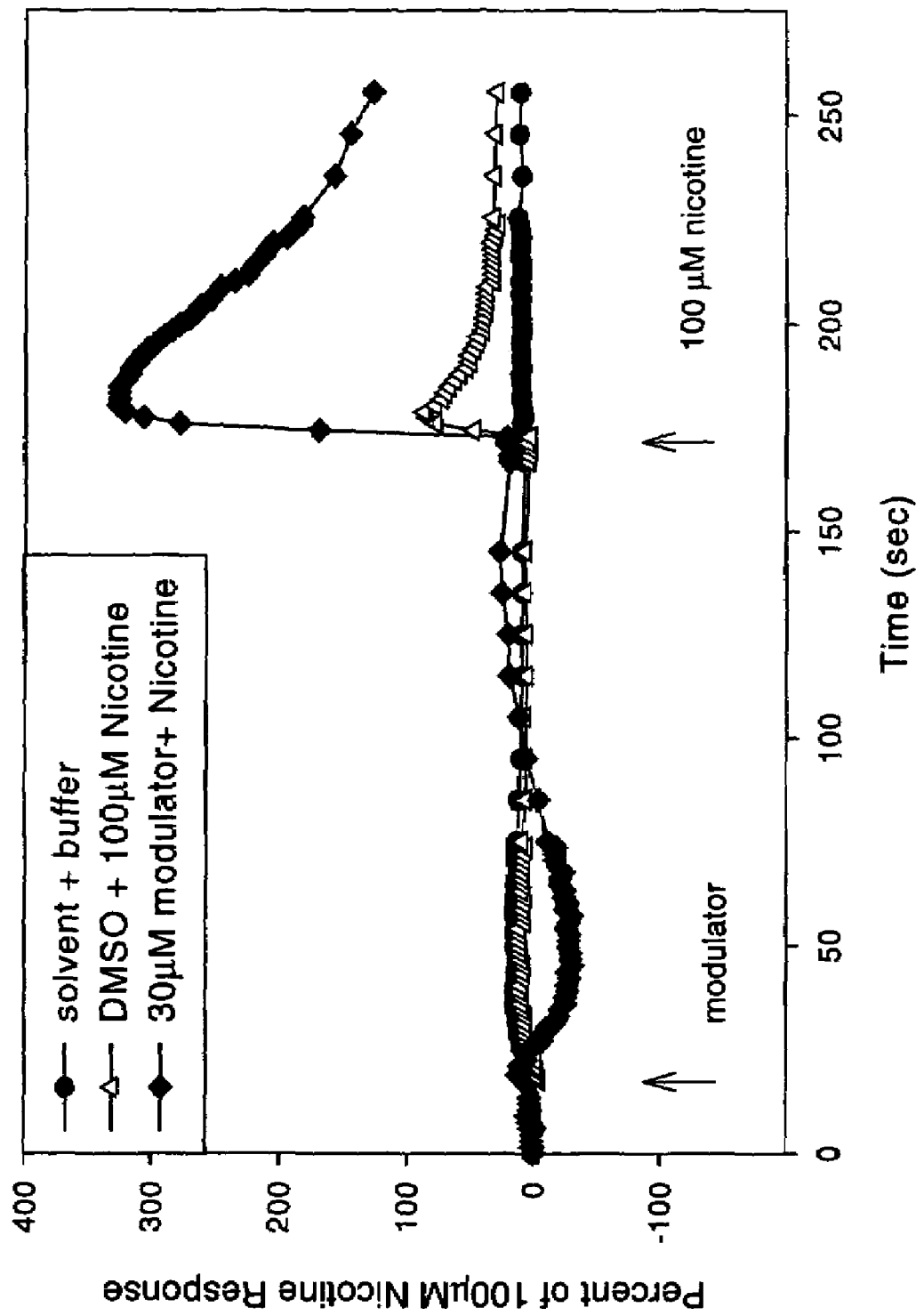

The SH-EP1 cells expressing the double mutation of SEQ ID NO: 13 (double mutant SHEP cells) were grown in minimal essential medium (MEM) containing nonessential amino acids supplemented with 10% fetal bovine serum, L-glutamine, 100 units/ml penicillin/streptomycin, 250 ng/ml fungizone, u400 g/ml Hygromycin-B, and 800 ug/ml Geneticin. The cells were grown in a 37° C. incubator with 6% $CO_2$. The cells were trypsinized and plated in 96 well plates with dark side walls and clear bottoms (Coming # 3614) at density of 2 6×10$^4$ cells per well two days before analysis. The double mutant SHEP cells were loaded in a 1:1 mixture of 2 mM Calcium Green-1, AM (Molecular Probes) prepared in anhydrous dimethylsulfoxide and 20% pluronic F-127 (Molecular Probes). This reagent was added directly to the growth medium of each well to achieve a final concentration of 2 M of Calcium Green-1, AM. The double mutant SHEP cells were incubated in the dye for one hour at 37° C. and then washed with 4 cycles of Bio-Tek plate washer. Each cycle was programmed to wash each well with four times with either EBSS or MMEBSS. After the third cycle, the double mutant-SHEP cells were allowed to incubate at 37° C. for at least ten minutes. After the fourth cycle final volume in each well was 100 ul. Allosteric modulator activity was measured as the drug dependent increase in the agonist activity using the double mutant AChR channel as a drug target. Modulator induce increase in agonist activity was measured by increasing intracellular calcium accumulation. FLIPR (Molecular Devices) was set up to excite Calcium Green with at 488 nanometer using 500 mW of power and reading fluorescence emission above 525 nanometers. A 0.5 second exposure was used to illuminate each well. Fluorescence was detected using a F-stop set of either 2.0 or 1.2. Specifically, after 30 seconds of baseline recording, test compounds were added to each well of a 96 well plate using a 50 l from a 3× drug stock. In each experiment, 4 wells were used as solvent controls. As indicated in FIG. 10 modulator activity produced an increase in the nicotine-induced influx of intracellular calcium. The preferred modulator had no effect in the absence of agonist. All data is plotted relative to the effect of 100 M nicotine, which induced a maximal calcium influx.

EXAMPLE 8

Changing the ionic conditions of cellular medium is also likely to increase the calcium influx on many other ion channels that do not conduct calcium under physiological conditions. For example, it is known that the P2X(2) family of purinoceptors are cation-selective channels that are activated by ATP and its analogues. The ionic selectivity of this channel is $K^+>Rb^+>Cs^+>Na^+>Li^+>>>Ca^{++}$. In addition, divalent ions such induce a block of the channel that is measured by a reduction in amplitude of the unitary currents. Organic cations such as NMDG(+), Tris(+), TMA(+) and TEA(+) are virtually impermeant. It is likely that the ionic composition of MMEBSS will establish conditions that will permit $Ca^{++}$ ions to pass through the channel in sufficient quantities to use a calcium influx assay to measure channel activity. Under these conditions, a calcium influx assay can be used as a high throughput assay using P2X receptors as a drug target.

While the present invention has been described in terms of specific embodiments, it is understood that variations and modifications will occur to those in the art, all of which are intended as aspects of the invention. Accordingly only such limitations as appear in the claims should be placed in the invention.

What is claimed is:

1. An isolated polypeptide comprising the amino acid sequence set forth in SEQ ID NO: 14, wherein:
    (1) either the proline residue at position 230 has been replaced with an amino acid residue selected from the group consisting of glycine, alanine, isoleucine, leucine, and valine, or the serine residue present at position 241 has been replaced with an amino acid residue selected from the group consisting of threonine, methionine, asparagine, glutamine, and tyrosine; or
    (2) both the proline residue at position 230 has been replaced with an amino acid residue selected from the group consisting of glycine, alanine, isoleucine, leucine, and valine, and the serine residue present at position 241 has been replaced with an amino acid residue selected from the group consisting of threonine, methionine, asparagine, glutamine, and tyrosine,
    and wherein said polypeptide, when produced in a recombinant SH-EP1 cell that contains an encoding DNA sequence for said polypeptide, evidences increased intracellular calcium accumulation in the presence of nicotine as agonist.

2. An isolated polypeptide comprising residues 23 through 502 of SEQ ID NO: 14, wherein:
    (1) either the proline residue at position 230 has been replaced with an amino acid residue selected from the group consisting of glycine, alanine, isoleucine, leucine, and valine, or the serine residue present at position 241 has been replaced with an amino acid residue selected from the group consisting of threonine, methionine, asparagine, glutamine, and tyrosine; or
    (2) both the proline residue at position 230 has been replaced with an amino acid residue selected from the group consisting of glycine, alanine, isoleucine, leucine, and valine, and the serine residue present at position 241 has been replaced with an amino acid residue selected from the group consisting of threonine, methionine, asparagine, glutamine, and tyrosine,
    and wherein said polypeptide, when produced in a recombinant SH-EP1 cell that contains an encoding DNA sequence for said polypeptide, evidences increased intracellular calcium accumulation in the presence of nicotine as agonist.

3. An isolated cell that expresses the polypeptide of claim 1.

4. An isolated cell that expresses the polypeptide of claim 2.

* * * * *

```
                              SEQUENCE LISTING

<160> NUMBER OF SEQ ID NOS: 14

<210> SEQ ID NO 1
<211> LENGTH: 1509
<212> TYPE: DNA
<213> ORGANISM: Homo sapiens

<400> SEQUENCE: 1
atgcgctgct cgccgggagg cgtctggctg gcgctggccg cgtcgctcct gcacgtgtcc     60
ctgcaaggcg agttccagag gaagctttac aaggagctgg tcaagaacta caatcccttg    120
gagaggcccg tggccaatga ctcgcaacca ctcaccgtct acttctccct gagcctcctg    180
cagatcatgg acgtggatga agaaccaa gttttaacca ccaacatttg gctgcaaatg    240
tcttggacag atcactattt acagtggaat gtgtcagaat atccagggt gaagactgtt    300 cgtttcccag atggccagat ttggaaacca gacattcttc tctataacag tgctgatgag    360 cgcttttgacg ccacattcca cactaacgtg ttggtgaatt cttctgggca ttgccagtac    420
ctgcctccag gcatattcaa gagttcctgc tacatcgatg tacgctggtt tccctttgat    480
gtgcagcact gcaaactgaa gtttgggtcc tggtcttacg gaggctggtc cttggatctg    540
cagatgcagg aggcagatat cagtggctat atccccaatg gagaatggga cctagtggga    600
atccccggca gaggagtga aaggttctat gagtgctgca aagagcccta ccccgatgtc    660
accttcacag tgaccatgcg ccgcaggacg ctctactatg gcctcaacct gctgatcccc    720
tgtgtgctca tctccgccct cgccctgctg gtgttcctgc ttcctgcaga ttccggggag    780
aagatttccc tggggataac agtcttactc tctcttaccg tcttcatgct gctcgtggct    840
gagatcatgc ccgcaacatc cgattcggta ccattgatag cccagtactt cgccagcacc    900
atgatcatcg tgggcctctc ggtggtggtg acggtgatcg tgctgcagta ccaccaccac    960
gaccccgacg ggcaagat gcccaagtgg accagagtca tccttctgaa ctggtgcgcg   1020
tggttcctgc gaatgaagag gccgggggag gacaaggtgc gccggcctg ccagcacaag   1080 cagcggcgct gcagcctggc cagtgtggag atgagcgccg tggcgccgcc gcccgccagc   1140
aacgggaacc tgctgtacat cggcttccgc ggcctggacg cgtgcactg tgtcccgacc   1200 cccgactctg gggtagtgtg tggccgcatg gcctgctccc ccacgcacga tgagcacctc   1260
ctgcacggcg ggcaaccccc cgaggggac ccggacttgg ccaagatcct ggaggaggtc   1320
```

-continued

```
cgctacattg ccaatcgctt ccgctgccag gacgaaagcg aggcggtctg cagcgagtgg      1380
aagttcgccg cctgtgtggt ggaccgcctg tgcctcatgg ccttctcggt cttcaccatc      1440
atctgcacca tcggcatcct gatgtcggct cccaacttcg tggaggccgt gtccaaagac      1500
tttgcgtaa                                                              1509
```

<210> SEQ ID NO 2
<211> LENGTH: 502
<212> TYPE: PRT
<213> ORGANISM: Homo sapiens

<400> SEQUENCE: 2

```
Met Arg Cys Ser Pro Gly Gly Val Trp Leu Ala Leu Ala Ala Ser Leu
  1               5                  10                  15

Leu His Val Ser Leu Gln Gly Glu Phe Gln Arg Lys Leu Tyr Lys Glu
                 20                  25                  30

Leu Val Lys Asn Tyr Asn Pro Leu Glu Arg Pro Val Ala Asn Asp Ser
             35                  40                  45

Gln Pro Leu Thr Val Tyr Phe Ser Leu Ser Leu Leu Gln Ile Met Asp
     50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
        275                 280                 285

Ser Val Pro Leu Ile Ala Gln Tyr Phe Ala Ser Thr Met Ile Ile Val
    290                 295                 300

Gly Leu Ser Val Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335
```

```
Asn Trp Cys Ala Trp Phe Leu Arg Met Lys Arg Pro Gly Glu Asp Lys
            340                 345                 350

Val Arg Pro Ala Cys Gln His Lys Gln Arg Arg Cys Ser Leu Ala Ser
            355                 360                 365

Val Glu Met Ser Ala Val Ala Pro Pro Ala Ser Asn Gly Asn Leu
        370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
            420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500

<210> SEQ ID NO 3
<211> LENGTH: 1464
<212> TYPE: DNA
<213> ORGANISM: Mus musculus

<400> SEQUENCE: 3
atgcggctct gcatcccgca ggtgctgttg gccttgttcc tttccatgct gacagccccg      60
ggagaaggca gccggaggag ggccacccag gaggatacca cccagcctgc tctactaagg     120
ctgtcagacc acctcctggc taactacaag aaggggtgc ggcctgtgcg ggactggagg      180
aagcctacta ctgtctccat tgatgtcatc atgtatgcca cctcaacgt ggatgagaag      240 aaccaggttc tgaccaccta catatggtac cggcagtact ggactgatga gtttctgcag     300
tggactcctg aggacttcga caatgtcacc aaattgtcca tccccacaga cagcatctgg     360
gtccctgaca ttctcatcaa tgagtttgtg acgtgggga gtctccgaa cattccttat       420 gtgtacgtgc atcatcgagg tgaagttcag aactacaagc ccttgcaatt ggtgaccgcc     480
tgtagccttg acatctacaa cttccccttt gatgtgcaga actgttctct gactttcacc     540
agctggctgc acaccatcca ggacatcaac attactctgt ggcgatcacc ggaagaagtg     600
aggtctgaca gagcatcttt cataaatcag ggcgagtggg agctgctgga ggtgttcccc     660
cagttcaagg agttcagcat agatatcagt aacagctatg cagaaatgaa gttctacgtg     720
atcatccgcc ggaggccttt attctatgca gtcagcctct gctgcccag tatcttcctc      780 atggtcgtgg acattgtggg cttttgcctg ccccggaca gtggtgagag agtctctttc      840
aagatcacac tccttctggg atactcagtc ttcctcatca tcgtgtcaga cacactgccg     900
gcaacgatcg gtaccccct cattggtgtc actttgtgg tgtgcatggc tctgctagtg       960
ataagcctcg ctgagaccat cttcattgtg cggctggtgc ataagcagga cctacagcgg    1020
ccagtacctg actggctgag gcacctggtc tagacagaa tagcctggat actctgccta     1080
ggggagcagc ctatggccca tagaccccca gccaccttcc aagccaacaa gactgatgac    1140
```

```
tgctcaggtt ctgatcttct tccagccatg ggaaaccact gcagccatgt tggaggacct    1200
caggacttgg agaagacccc aagggcaga ggtagccctc ttccaccacc aagggaggcc    1260
tcactggctg tgcgtggtct cttgcaagag ctatcctcca tccgccactt cctggagaag    1320
cgggatgaga tgcgggaggt ggcaagggac tggctgcggg tgggatacgt gctggacagg    1380
ctgctgttcc gcatctacct gctggctgtg ctcgcttaca gcatcaccct ggtcactctc    1440
tggtccattt ggcattattc ttga                                           1464
```

<210> SEQ ID NO 4
<211> LENGTH: 457
<212> TYPE: PRT
<213> ORGANISM: Mus musculus

<400> SEQUENCE: 4

```
Glu Asp Thr Thr Gln Pro Ala Leu Leu Arg Leu Ser Asp His Leu Leu
 1               5                  10                  15

Ala Asn Tyr Lys Lys Gly Val Arg Pro Val Arg Asp Trp Arg Lys Pro
            20                  25                  30

Thr Thr Val Ser Ile Asp Val Ile Met Tyr Ala Ile Leu Asn Val Asp
        35                  40                  45

Glu Lys Asn Gln Val Leu Thr Thr Tyr Ile Trp Tyr Arg Gln Tyr Trp
    50                  55                  60

Thr Asp Glu Phe Leu Gln Trp Thr Pro Glu Asp Phe Asp Asn Val Thr
65                  70                  75                  80

Lys Leu Ser Ile Pro Thr Asp Ser Ile Trp Val Pro Asp Ile Leu Ile
                85                  90                  95

Asn Glu Phe Val Asp Val Gly Lys Ser Pro Asn Ile Pro Tyr Val Tyr
            100                 105                 110

Val His His Arg Gly Glu Val Gln Asn Tyr Lys Pro Leu Gln Leu Val
        115                 120                 125

Thr Ala Cys Ser Leu Asp Ile Tyr Asn Phe Pro Phe Asp Val Gln Asn
    130                 135                 140

Cys Ser Leu Thr Phe Thr Ser Trp Leu His Thr Ile Gln Asp Ile Asn
145                 150                 155                 160

Ile Thr Leu Trp Arg Ser Pro Glu Glu Val Arg Ser Asp Lys Ser Ile
                165                 170                 175

Phe Ile Asn Gln Gly Glu Trp Glu Leu Leu Glu Val Phe Pro Gln Phe
            180                 185                 190

Lys Glu Phe Ser Ile Asp Ile Ser Asn Ser Tyr Ala Glu Met Lys Phe
        195                 200                 205

Tyr Val Ile Ile Arg Arg Arg Pro Leu Phe Tyr Ala Val Ser Leu Leu
    210                 215                 220

Leu Pro Ser Ile Phe Leu Met Val Val Asp Ile Val Gly Phe Cys Leu
225                 230                 235                 240

Pro Pro Asp Ser Gly Glu Arg Val Ser Phe Lys Ile Thr Leu Leu Leu
                245                 250                 255

Gly Tyr Ser Val Phe Leu Ile Ile Val Ser Asp Thr Leu Pro Ala Thr
            260                 265                 270

Ile Gly Thr Pro Leu Ile Gly Val Tyr Phe Val Val Cys Met Ala Leu
        275                 280                 285

Leu Val Ile Ser Leu Ala Glu Thr Ile Phe Ile Val Arg Leu Val His
    290                 295                 300

Lys Gln Asp Leu Gln Arg Pro Val Pro Asp Trp Leu Arg His Leu Val
305                 310                 315                 320
```

```
Leu Asp Arg Ile Ala Trp Ile Leu Cys Leu Gly Glu Gln Pro Met Ala
            325                 330                 335

His Arg Pro Pro Ala Thr Phe Gln Ala Asn Lys Thr Asp Asp Cys Ser
            340                 345                 350

Gly Ser Asp Leu Leu Pro Ala Met Gly Asn His Cys Ser His Val Gly
            355                 360                 365

Gly Pro Gln Asp Leu Glu Lys Thr Pro Arg Gly Arg Gly Ser Pro Leu
        370                 375                 380

Pro Pro Pro Arg Glu Ala Ser Leu Ala Val Arg Gly Leu Leu Gln Glu
385                 390                 395                 400

Leu Ser Ser Ile Arg His Phe Leu Glu Lys Arg Asp Glu Met Arg Glu
            405                 410                 415

Val Ala Arg Asp Trp Leu Arg Val Gly Tyr Val Leu Asp Arg Leu Leu
            420                 425                 430

Phe Arg Ile Tyr Leu Leu Ala Val Leu Ala Tyr Ser Ile Thr Leu Val
        435                 440                 445

Thr Leu Trp Ser Ile Trp His Tyr Ser
    450                 455

<210> SEQ ID NO 5
<211> LENGTH: 1416
<212> TYPE: DNA
<213> ORGANISM: Artificial Sequence
<220> FEATURE:
<223> OTHER INFORMATION: Description of Artificial Sequence: human/mouse
      hybrid sequence

<400> SEQUENCE: 5
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga agaaccaa gttttaacca ccaacatttg gctgcaaatg      240
tcttggacaa tcactatttt acagtggaat gtgtcagaat atccagggtt gaagactgtt     300
cgtttcccag atggccagat ttggaaacca gacattcttc tctataacag tgctgatgag     360
cgctttgacg ccacattcca cactaacgtg ttggtgaatt cttctgggca ttgccagtac     420
ctgcctccag gcatattcaa gagttcctgc tacatcgatg tacgctggtt tccctttgat     480
gtgcagcact gcaaactgaa gtttgggtcc tggtcttacg gaggctggtc cttggatctg     540
cagatgcagg aggcagatat cagtggctat atccccaatg agaatggga cctagtggga     600 atccccggca agaggagtga aaggttctat gagtgctgca agagcccta ccccgatgtc     660 accttcacag tgaccatgcg ccgcaggacg ttattctatg cagtcagcct cttgctgccc     720
agtatcttcc tcatggtcgt ggacattgtg ggcttttgcc tgccccggga cagtggtgag     780
agagtctctt tcaagatcac actccttctg ggatactcag tcttcctcat catcgtgtca     840
gacacactgc cggcaacgat cggtaccccc tcattggtg tctactttgt ggtgtgcatg     900
gctctgctag tgataagcct cgctgagacc atcttcattg tgcggctggt gcataagcag     960
gacctacagc ggccagtacc tgactggctg aggcacctgg tcctagacag aatagcctgg    1020
atactctgcc tagggagca gcctatggcc catagacccc cagccacctt ccaagccaac    1080
aagactgatg actgctcagg ttctgatctt cttccagcca tgggaaacca ctgcagccat    1140
gttggaggac tcaggactt ggagaagacc ccaagggca gaggtagccc tcttccacca    1200
```

-continued

```
ccaagggagg cctcactggc tgtgcgtggt ctcttgcaag agctatcctc catccgccac   1260
ttcctggaga agcgggatga gatgcggag gtggcaaggg actggctgcg ggtgggatac   1320
gtgctggaca ggctgctgtt ccgcatctac ctgctggctg tgctcgctta cagcatcacc   1380
ctggtcactc tctggtccat ttggcattat tcttga                              1416
```

<210> SEQ ID NO 6
<211> LENGTH: 470
<212> TYPE: PRT
<213> ORGANISM: Artificial Sequence
<220> FEATURE:
<223> OTHER INFORMATION: Description of Artificial Sequence: human/mouse hybrid sequence

<400> SEQUENCE: 6

```
Met Arg Cys Ser Pro Gly Gly Val Trp Leu Ala Leu Ala Ala Ser Leu
  1               5                  10                  15

Leu His Val Ser Leu Gln Gly Glu Phe Gln Arg Lys Leu Tyr Lys Glu
                 20                  25                  30

Leu Val Lys Asn Tyr Asn Pro Leu Glu Arg Pro Val Ala Asn Asp Ser
             35                  40                  45

Gln Pro Leu Thr Val Tyr Phe Ser Leu Ser Leu Leu Gln Ile Met Asp
         50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Ile Ile Arg Arg Arg Pro Phe Tyr Ala Val Ser Leu Leu Leu Pro Ser
225                 230                 235                 240

Ile Phe Leu Met Val Val Asp Ile Val Gly Phe Cys Leu Pro Pro Asp
                245                 250                 255

Ser Gly Glu Arg Val Ser Phe Lys Ile Thr Leu Leu Leu Gly Tyr Ser
            260                 265                 270

Val Phe Leu Ile Ile Val Ser Asp Thr Leu Pro Ala Thr Ile Gly Thr
        275                 280                 285

Pro Leu Ile Gly Val Tyr Phe Val Val Cys Met Ala Leu Leu Val Ile
    290                 295                 300

Ser Leu Ala Glu Thr Ile Phe Ile Val Arg Leu Val His Lys Gln Asp
305                 310                 315                 320
```

```
Leu Gln Arg Pro Val Pro Asp Trp Leu Arg His Leu Val Leu Asp Arg
                325                 330                 335

Ile Ala Trp Ile Leu Cys Leu Gly Glu Gln Pro Met Ala His Arg Pro
            340                 345                 350

Pro Ala Thr Phe Gln Ala Asn Lys Thr Asp Asp Cys Ser Gly Ser Asp
        355                 360                 365

Leu Leu Pro Ala Met Gly Asn His Cys Ser His Val Gly Gly Pro Gln
    370                 375                 380

Asp Leu Glu Lys Thr Pro Arg Gly Arg Gly Ser Pro Leu Pro Pro Pro
385                 390                 395                 400

Arg Glu Ala Ser Leu Ala Val Arg Gly Leu Leu Gln Glu Leu Ser Ser
                405                 410                 415

Ile Arg His Phe Leu Glu Lys Arg Asp Glu Met Arg Glu Val Ala Arg
            420                 425                 430

Asp Trp Leu Arg Val Gly Tyr Val Leu Asp Arg Leu Leu Phe Arg Ile
        435                 440                 445

Tyr Leu Leu Ala Val Leu Ala Tyr Ser Ile Thr Leu Val Thr Leu Trp
    450                 455                 460

Ser Ile Trp His Tyr Ser
465                 470

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence:GG443 PCR
                        Primer

<400> SEQUENCE: 7
ggctctagac caccatgcgc tgttcaccgg gaggcgtctg gctg                   44

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:GG444 PCR
                        Primer

<400> SEQUENCE: 8
gggtgatcac tgtgaaggtg acatcagggt agggctc                          37

<210> SEQ ID NO 9
<211> LENGTH: 1509
<212> TYPE: DNA
<213> ORGANISM: Homo sapiens

<400> SEQUENCE: 9
atgcgctgct cgccgggagg cgtctggctg gcgctggccg cgtcgctcct gcacgtgtcc    60
ctgcaaggcg agttccagag gaagctttac aaggagctgg tcaagaacta caatcccttg   120
gagaggcccg tggccaatga ctcgcaacca ctcaccgtct acttctccct gagcctcctg   180
cagatcatgg acgtggatga agaaccaa gttttaacca ccaacatttg gctgcaaatg   240
tcttggacaa tcactatttt acagtggaat gtgtcagaat atccaggggt gaagactgtt   300
cgtttcccag atggccagat ttggaaacca gacattcttc tctataacag tgctgatgag   360
cgctttgacg ccacattcca cactaacgtg ttggtgaatt cttctgggca ttgccagtac   420
ctgcctccag gcatattcaa gagttcctgc tacatcgatg tacgctggtt tccctttgat   480
```

-continued

```
gtgcagcact gcaaactgaa gtttgggtcc tggtcttacg gaggctggtc cttggatctg        540
cagatgcagg aggcagatat cagtggctat atccccaatg gagaatggga cctagtggga        600
atccccggca agaggagtga aaggttctat gagtgctgca aagagcccta ccccgatgtc        660
accttcacag tgaccatgcg ccgcaggccg ctctactatg cctcaacct gctgatcccc         720 tgtgtgctca tctccgccct cgccctgctg gtgttcctgc ttcctgcaga ttccggggag        780
aagatttccc tggggataac agtcttactc tctcttaccg tcttcatgct gctcgtggct        840
gagatcatgc ccgcaacatc cgattcggta ccattgatag cccagtactt cgccagcacc        900
atgatcatcg tgggcctctc ggtggtggtg acggtgatcg tgctgcagta ccaccaccac        960
gaccccgacg ggggcaagat gcccaagtgg accagagtca tccttctgaa ctggtgcgcg        1020
tggttcctgc gaatgaagag gcccggggag gacaaggtgc gcccggcctg ccagcacaag        1080
cagcggcgct gcagcctggc cagtgtggag atgagcgccg tggcgccgcc gcccgccagc        1140
aacgggaacc tgctgtacat cggcttccgc ggcctggacg gcgtgcactg tgtcccgacc        1200
cccgactctg gggtagtgtg tggccgcatg gcctgctccc ccacgcacga tgagcacctc        1260
ctgcacggcg ggcaacccc cgaggggggac ccggacttgg ccaagatcct ggaggaggtc       1320
cgctacattg ccaatcgctt ccgctgccag gacgaaagcg aggcggtctg cagcgagtgg       1380
aagttcgccg cctgtgtggt ggaccgcctg tgcctcatgg ccttctcggt cttcaccatc       1440
atctgcacca tcggcatcct gatgtcggct cccaacttcg tggaggccgt gtccaaagac       1500
tttgcgtaa                                                               1509
```

<210> SEQ ID NO 10
<211> LENGTH: 502
<212> TYPE: PRT
<213> ORGANISM: Homo sapiens

<400> SEQUENCE: 10

```
Met Arg Cys Ser Pro Gly Gly Val Trp Leu Ala Leu Ala Ala Ser Leu
 1               5                  10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
```

```
                    180             185             190
Asn Gly Glu Trp Asp Leu Val Gly Ile Pro Gly Lys Arg Ser Glu Arg
        195                 200                 205
Phe Tyr Glu Cys Cys Lys Glu Pro Tyr Pro Asp Val Thr Phe Thr Val
210                 215                 220
Thr Met Arg Arg Pro Leu Tyr Tyr Gly Leu Asn Leu Leu Ile Pro
225                 230                 235                 240
Cys Val Leu Ile Ser Ala Leu Ala Leu Leu Val Phe Leu Leu Pro Ala
                245                 250                 255
Asp Ser Gly Glu Lys Ile Ser Leu Gly Ile Thr Val Leu Leu Ser Leu
            260                 265                 270
Thr Val Phe Met Leu Leu Val Ala Glu Ile Met Pro Ala Thr Ser Asp
            275                 280                 285
Ser Val Pro Leu Ile Ala Gln Tyr Phe Ala Ser Thr Met Ile Ile Val
        290                 295                 300
Gly Leu Ser Val Val Thr Val Ile Val Leu Gln Tyr His His His
305                 310                 315                 320
Asp Pro Asp Gly Gly Lys Met Pro Lys Trp Thr Arg Val Ile Leu Leu
                325                 330                 335
Asn Trp Cys Ala Trp Phe Leu Arg Met Lys Arg Pro Gly Glu Asp Lys
            340                 345                 350
Val Arg Pro Ala Cys Gln His Lys Gln Arg Arg Cys Ser Leu Ala Ser
        355                 360                 365
Val Glu Met Ser Ala Val Ala Pro Pro Ala Ser Asn Gly Asn Leu
    370                 375                 380
Leu Tyr Ile Gly Phe Arg Gly Leu Asp Gly Val His Cys Val Pro Thr
385                 390                 395                 400
Pro Asp Ser Gly Val Val Cys Gly Arg Met Ala Cys Ser Pro Thr His
                405                 410                 415
Asp Glu His Leu Leu His Gly Gly Gln Pro Pro Glu Gly Asp Pro Asp
            420                 425                 430
Leu Ala Lys Ile Leu Glu Glu Val Arg Tyr Ile Ala Asn Arg Phe Arg
            435                 440                 445
Cys Gln Asp Glu Ser Glu Ala Val Cys Ser Glu Trp Lys Phe Ala Ala
    450                 455                 460
Cys Val Val Asp Arg Leu Cys Leu Met Ala Phe Ser Val Phe Thr Ile
465                 470                 475                 480
Ile Cys Thr Ile Gly Ile Leu Met Ser Ala Pro Asn Phe Val Glu Ala
                485                 490                 495
Val Ser Lys Asp Phe Ala
            500

<210> SEQ ID NO 11
<211> LENGTH: 1509
<212> TYPE: DNA
<213> ORGANISM: Homo sapiens

<400> SEQUENCE: 11
atgcgctgct cgccgggagg cgtctggctg gcgctggccg cgtcgctcct gcacgtgtcc    60
ctgcaaggcg agttccagag gaagctttac aaggagctgg tcaagaacta caatcccttg   120
gagaggcccg tggccaatga ctcgcaacca ctcaccgtct acttctccct gagcctcctg   180
cagatcatgg acgtggatga gaagaaccaa gttttaacca ccaacatttg gctgcaaatg   240
tcttggacag atcactattt acagtggaat gtgtcagaat atccaggggt gaagactgtt   300
```

-continued

```
cgtttcccag atggccagat ttggaaacca gacattcttc tctataacag tgctgatgag    360
cgctttgacg ccacattcca cactaacgtg ttggtgaatt cttctgggca ttgccagtac    420
ctgcctccag gcatattcaa gagttcctgc tacatcgatg tacgctggtt tccctttgat    480
gtgcagcact gcaaactgaa gtttgggtcc tggtcttacg gaggctggtc cttggatctg    540
cagatgcagg aggcagatat cagtggctat atccccaatg gagaatggga cctagtggga    600
atccccggca agaggagtga aaggttctat gagtgctgca agagcccta ccccgatgtc     660
accttcacag tgaccatgcg ccgcaggacg ctctactatg ccctcaacct gctgatcccc    720
agtgtgctca tctccgccct cgccctgctg gtgttcctgc ttcctgcaga ttccggggag    780
aagatttccc tggggataac agtcttactc tctcttaccg tcttcatgct gctcgtggct    840
gagatcatgc ccgcaacatc cgattcggta ccattgatag cccagtactt cgccagcacc    900
atgatcatcg tgggcctctc ggtggtggtg acggtgatcg tgctgcagta ccaccaccac    960
gaccccgacg ggggcaagat gcccaagtgg accagagtca tccttctgaa ctggtgcgcg    1020
tggttcctgc gaatgaagag gcccggggag gacaaggtgc gccggcctg ccagcacaag     1080
cagcggcgct gcagcctggc cagtgtggag atgagcgccg tggcgccgcc gcccgccagc    1140
aacgggaacc tgctgtacat cggcttccgc ggcctggacg gcgtgcactg tgtcccgacc    1200
cccgactctg gggtagtgtg tggccgcatg gcctgctccc ccacgcacga tgagcacctc    1260
ctgcacggcg gcaaccccc cgaggggac ccggacttgg ccaagatcct ggaggaggtc      1320
cgctacattg ccaatcgctt ccgctgccag gacgaaagcg aggcggtctg cagcgagtgg    1380
aagttcgccg cctgtgtggt ggaccgcctg tgcctcatgg ccttctcggt cttcaccatc    1440
atctgcacca tcggcatcct gatgtcggct cccaacttcg tggaggccgt gtccaaagac    1500
tttgcgtaa                                                            1509
```

<210> SEQ ID NO 12
<211> LENGTH: 502
<212> TYPE: PRT
<213> ORGANISM: Homo sapiens

<400> SEQUENCE: 12

```
Met Arg Cys Ser Pro Gly Gly Val Trp Leu Ala Leu Ala Ala Ser Leu
 1               5                  10                  15

Leu His Val Ser Leu Gln Gly Glu Phe Gln Arg Lys Leu Tyr Lys Glu
             20                  25                  30

Leu Val Lys Asn Tyr Asn Pro Leu Glu Arg Pro Val Ala Asn Asp Ser
         35                  40                  45

Gln Pro Leu Thr Val Tyr Phe Ser Leu Ser Leu Gln Ile Met Asp
     50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
```

```
                145                 150                 155                 160
        Val Gln His Cys Lys Leu Lys Phe Gly Ser Trp Ser Tyr Gly Gly Trp
                        165                 170                 175

Ser Leu Asp Leu Gln Met Gln Glu Ala Asp Ile Ser Gly Tyr Ile Pro
                    180                 185                 190

Asn Gly Glu Trp Asp Leu Val Gly Ile Pro Gly Lys Arg Ser Glu Arg
                195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Gly Leu Asn Leu Leu Ile Pro
        225                 230                 235                 240

Ser Val Leu Ile Ser Ala Leu Ala Leu Leu Val Phe Leu Leu Pro Ala
                        245                 250                 255

Asp Ser Gly Glu Lys Ile Ser Leu Gly Ile Thr Val Leu Leu Ser Leu
                    260                 265                 270

Thr Val Phe Met Leu Leu Val Ala Glu Ile Met Pro Ala Thr Ser Asp
                275                 280                 285

Ser Val Pro Leu Ile Ala Gln Tyr Phe Ala Ser Thr Met Ile Ile Val
            290                 295                 300

Gly Leu Ser Val Val Thr Val Ile Val Leu Gln Tyr His His His
        305                 310                 315                 320

Asp Pro Asp Gly Gly Lys Met Pro Lys Trp Thr Arg Val Ile Leu Leu
                        325                 330                 335

Asn Trp Cys Ala Trp Phe Leu Arg Met Lys Arg Pro Gly Glu Asp Lys
                    340                 345                 350

Val Arg Pro Ala Cys Gln His Lys Gln Arg Arg Cys Ser Leu Ala Ser
                355                 360                 365

Val Glu Met Ser Ala Val Ala Pro Pro Ala Ser Asn Gly Asn Leu
            370                 375                 380

Leu Tyr Ile Gly Phe Arg Gly Leu Asp Gly Val His Cys Val Pro Thr
        385                 390                 395                 400

Pro Asp Ser Gly Val Val Cys Gly Arg Met Ala Cys Ser Pro Thr His
                        405                 410                 415

Asp Glu His Leu Leu His Gly Gly Gln Pro Pro Glu Gly Asp Pro Asp
                    420                 425                 430

Leu Ala Lys Ile Leu Glu Glu Val Arg Tyr Ile Ala Asn Arg Phe Arg
                435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
        465                 470                 475                 480

Ile Cys Thr Ile Gly Ile Leu Met Ser Ala Pro Asn Phe Val Glu Ala
                        485                 490                 495

Val Ser Lys Asp Phe Ala
                    500

<210> SEQ ID NO 13
<211> LENGTH: 1509
<212> TYPE: DNA
<213> ORGANISM: Homo sapiens

<400> SEQUENCE: 13
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
```

-continued

```
gagaggcccg tggccaatga ctcgcaacca ctcaccgtct acttctccct gagcctcctg      180
cagatcatgg acgtggatga agaaccaa  gttttaacca ccaacatttg gctgcaaatg      240
tcttggacag atcactattt acagtggaat gtgtcagaat atccagggg  gaagactgtt      300 cgtttcccag atggccagat ttggaaacca gacattcttc tctataacag tgctgatgag      360
cgctttgacg ccacattcca cactaacgtg ttggtgaatt cttctgggca ttgccagtac      420
ctgcctccag gcatattcaa gagttcctgc tacatcgatg tacgctggtt tccctttgat      480
gtgcagcact gcaaactgaa gtttgggtcc tggtcttacg gaggctggtc cttggatctg      540
cagatgcagg aggcagatat cagtggctat atccccaatg gagaatggga cctagtggga      600
atccccggca agaggagtga aaggttctat gagtgctgca aagagcccta ccccgatgtc      660
accttcacag tgaccatgcg ccgcaggccg ctctactatg cctcaacct  gctgatcccc      720 agtgtgctca tctccgccct cgccctgctg gtgttcctgc ttcctgcaga ttccggggag      780
aagatttccc tggggataac agtcttactc tctcttaccg tcttcatgct gctcgtggct      840
gagatcatgc ccgcaacatc cgattcggta ccattgatag cccagtactt cgccagcacc      900
atgatcatcg tgggcctctc ggtggtggtg acggtgatcg tgctgcagta ccaccaccac      960
gaccccgacg gggcaagat  gcccaagtgg accagagtca tccttctgaa ctggtgcgcg     1020
tggttcctgc gaatgaagag gccgggggag gacaaggtgc gcccggcctg ccagcacaag     1080
cagcggcgct gcagcctggc cagtgtggag atgagcgccg tggcgccgcc gcccgccagc     1140
aacgggaacc tgctgtacat cggcttccgc ggcctggacg gcgtgcactg tgtcccgacc     1200
cccgactctg ggtagtgtg  tggccgcatg gcctgctccc ccacgcacga tgagcacctc     1260
ctgcacggcg gcaaccccc  cgagggggac ccggacttgg ccaagatcct ggaggaggtc     1320
cgctacattg ccaatcgctt ccgctgccag gacgaaagcg aggcggtctg cagcgagtgg     1380
aagttcgccg cctgtgtggt ggaccgcctg tgcctcatgg ccttctcggt cttcaccatc     1440
atctgcacca tcggcatcct gatgtcggct cccaacttcg tggaggccgt gtccaaagac     1500
tttgcgtaa                                                             1509
```

<210> SEQ ID NO 14
<211> LENGTH: 502
<212> TYPE: PRT
<213> ORGANISM: Homo sapiens

<400> SEQUENCE: 14

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
```

```
            115                 120                 125
Asn Val Leu Val Asn Ser Ser Gly His Cys Gln Tyr Leu Pro Pro Gly
            130                 135                 140
Ile Phe Lys Ser Ser Cys Tyr Ile Asp Val Arg Trp Phe Pro Phe Asp
145                 150                 155                 160
Val Gln His Cys Lys Leu Lys Phe Gly Ser Trp Ser Tyr Gly Gly Trp
                    165                 170                 175
Ser Leu Asp Leu Gln Met Gln Glu Ala Asp Ile Ser Gly Tyr Ile Pro
                    180                 185                 190
Asn Gly Glu Trp Asp Leu Val Gly Ile Pro Gly Lys Arg Ser Glu Arg
                    195                 200                 205
Phe Tyr Glu Cys Cys Lys Glu Pro Tyr Pro Asp Val Thr Phe Thr Val
                    210                 215                 220
Thr Met Arg Arg Arg Pro Leu Tyr Tyr Gly Leu Asn Leu Leu Ile Pro
225                 230                 235                 240
Ser Val Leu Ile Ser Ala Leu Ala Leu Leu Val Phe Leu Leu Pro Ala
                        245                 250                 255
Asp Ser Gly Glu Lys Ile Ser Leu Gly Ile Thr Val Leu Leu Ser Leu
                    260                 265                 270
Thr Val Phe Met Leu Leu Val Ala Glu Ile Met Pro Ala Thr Ser Asp
                275                 280                 285
Ser Val Pro Leu Ile Ala Gln Tyr Phe Ala Ser Thr Met Ile Ile Val
                290                 295                 300
Gly Leu Ser Val Val Val Thr Val Ile Val Leu Gln Tyr His His His
305                 310                 315                 320
Asp Pro Asp Gly Gly Lys Met Pro Lys Trp Thr Arg Val Ile Leu Leu
                    325                 330                 335
Asn Trp Cys Ala Trp Phe Leu Arg Met Lys Arg Pro Gly Glu Asp Lys
                340                 345                 350
Val Arg Pro Ala Cys Gln His Lys Gln Arg Arg Cys Ser Leu Ala Ser
                355                 360                 365
Val Glu Met Ser Ala Val Ala Pro Pro Ala Ser Asn Gly Asn Leu
                370                 375                 380
Leu Tyr Ile Gly Phe Arg Gly Leu Asp Gly Val His Cys Val Pro Thr
385                 390                 395                 400
Pro Asp Ser Gly Val Val Cys Gly Arg Met Ala Cys Ser Pro Thr His
                    405                 410                 415
Asp Glu His Leu Leu His Gly Gly Gln Pro Pro Glu Gly Asp Pro Asp
                    420                 425                 430
Leu Ala Lys Ile Leu Glu Glu Val Arg Tyr Ile Ala Asn Arg Phe Arg
                    435                 440                 445
Cys Gln Asp Glu Ser Glu Ala Val Cys Ser Glu Trp Lys Phe Ala Ala
                450                 455                 460
Cys Val Val Asp Arg Leu Cys Leu Met Ala Phe Ser Val Phe Thr Ile
465                 470                 475                 480
Ile Cys Thr Ile Gly Ile Leu Met Ser Ala Pro Asn Phe Val Glu Ala
                    485                 490                 495
Val Ser Lys Asp Phe Ala
                500
```